(12) United States Patent
Jones et al.

(10) Patent No.: US 11,480,778 B2
(45) Date of Patent: Oct. 25, 2022

(54) AUTOMATED MICROSCOPIC CELL ANALYSIS

(71) Applicant: Medica Corporation, Bedford, MA (US)

(72) Inventors: Ronald Jones, Newton, NH (US); Adrian Gropper, Watertown, MA (US); Robert Hagopian, Belmont, MA (US); Charles Rogers, Halifax, MA (US); Thomas Vitella, Sandown, NH (US); Donald Barry, Jr., Groton, MA (US); Dirk Osterloh, Arlington, MA (US); Chen Yi, Boxborough, MA (US); Tyler Cote, Chelmsford, MA (US)

(73) Assignee: Medica Corporation, Bedford, MA (US)

( * ) Notice: Subject to any disclaimer, the term of this patent is extended or adjusted under 35 U.S.C. 154(b) by 0 days.

(21) Appl. No.: 16/434,067

(22) Filed: Jun. 6, 2019

(65) Prior Publication Data

US 2020/0174241 A1 Jun. 4, 2020

Related U.S. Application Data

(62) Division of application No. 14/947,971, filed on Nov. 20, 2015, now abandoned.

(Continued)

(51) Int. Cl.
| | |
|---|---|
| *G02B 21/16* | (2006.01) |
| *G01N 1/00* | (2006.01) |
| *G01N 1/38* | (2006.01) |
| *G01N 15/14* | (2006.01) |
| *G01N 1/31* | (2006.01) |

(Continued)

(52) U.S. Cl.
CPC ........ *G02B 21/16* (2013.01); *B01L 3/502715* (2013.01); *B01L 9/527* (2013.01);
(Continued)

(58) Field of Classification Search
CPC ......... G02B 21/16; B01L 9/527; G01N 1/312; G01N 15/1463; G01N 1/00
See application file for complete search history.

(56) References Cited

U.S. PATENT DOCUMENTS

| | | | |
|---|---|---|---|
| 3,756,783 | A | 9/1973 | Williams |
| 4,706,207 | A | 11/1987 | Hennessy et al. |

(Continued)

FOREIGN PATENT DOCUMENTS

| | | |
|---|---|---|
| CN | 100392403 | 6/2008 |
| WO | WO9952633 | 10/1999 |

(Continued)

OTHER PUBLICATIONS

"Comparison of image-based cell counting methods: Countess Automated Cell Counter vs. the hemocytometer", Invitrogen, 2009, pp. 1-4. (Year: 2009).*

(Continued)

*Primary Examiner* — Brian J. Sines
(74) *Attorney, Agent, or Firm* — Kristofer E. Elbing

(57) ABSTRACT

Disclosed in one aspect is a method for performing a complete blood count (CBC) on a sample of whole blood by metering a predetermined amount of the whole blood and mixing it with a predetermined amount of diluent and stain and transferring a portion thereof to an imaging chamber of fixed dimensions and utilizing an automated microscope with digital camera and cell counting and recognition software to count every white blood cell and red blood corpuscle and platelet in the sample diluent/stain mixture to determine the number of red cells, white cells, and platelets per unit (Continued)

volume, and analyzing the white cells with cell recognition software to classify them.

9 Claims, 23 Drawing Sheets

Related U.S. Application Data

(60) Provisional application No. 62/138,359, filed on Mar. 25, 2015, provisional application No. 62/113,360, filed on Feb. 6, 2015, provisional application No. 62/084,760, filed on Nov. 26, 2014.

(51) Int. Cl.
| | | |
|---|---|---|
| *B01L 3/00* | (2006.01) | |
| *G01N 35/00* | (2006.01) | |
| *B01L 9/00* | (2006.01) | |
| *G02B 21/34* | (2006.01) | |
| *G01N 15/10* | (2006.01) | |
| *G01N 15/00* | (2006.01) | |

(52) U.S. Cl.
CPC .............. *G01N 1/312* (2013.01); *G01N 1/38* (2013.01); *G01N 15/1463* (2013.01); *G01N 35/00069* (2013.01); *B01L 2200/04* (2013.01); *B01L 2200/0605* (2013.01); *B01L 2200/0684* (2013.01); *B01L 2200/0689* (2013.01); *B01L 2200/16* (2013.01); *B01L 2300/021* (2013.01); *B01L 2300/0654* (2013.01); *B01L 2300/0867* (2013.01); *B01L 2300/0883* (2013.01); *B01L 2300/123* (2013.01); *B01L 2300/161* (2013.01); *B01L 2400/049* (2013.01); *B01L 2400/0622* (2013.01); *B01L 2400/0644* (2013.01); *B01L 2400/0694* (2013.01); *G01N 2015/008* (2013.01); *G01N 2015/0073* (2013.01); *G01N 2015/1006* (2013.01); *G01N 2015/1486* (2013.01); *G01N 2035/00138* (2013.01); *G02B 21/34* (2013.01)

(56) References Cited

U.S. PATENT DOCUMENTS

| | | | |
|---|---|---|---|
| 5,352,585 | A | 10/1994 | Binder |
| 5,464,752 | A | 11/1995 | Kortright |
| 5,469,251 | A | 11/1995 | Kosaka |
| 5,486,335 | A | 1/1996 | Wilding |
| 5,891,734 | A | 4/1999 | Gill et al. |
| 6,082,185 | A | 7/2000 | Saaski |
| 6,235,536 | B1 | 5/2001 | Wardlaw |
| 6,251,615 | B1 | 6/2001 | Oberhardt |
| 6,656,683 | B1 | 12/2003 | Reuben |
| 6,811,668 | B1 | 11/2004 | Berndt |
| 7,553,453 | B2 | 6/2009 | Gu |
| 7,738,094 | B2 | 6/2010 | Goldberg |
| 7,764,821 | B2 | 7/2010 | Coumans |
| 7,771,658 | B2 | 8/2010 | Larsen |
| 7,797,990 | B2 | 9/2010 | Larsen et al. |
| 7,929,122 | B2 | 4/2011 | Wardlaw et al. |
| 8,028,566 | B2 | 10/2011 | Larsen |
| 8,067,245 | B2 | 11/2011 | van Ryper et al. |
| 8,211,701 | B2 | 7/2012 | Spence et al. |
| 8,221,985 | B2 | 7/2012 | Wardlaw et al. |
| 8,227,250 | B2 | 7/2012 | Larsen et al. |
| 8,241,572 | B2 | 8/2012 | Wardlaw |
| 8,310,658 | B2 | 11/2012 | Wardlaw et al. |
| 8,326,008 | B2 | 12/2012 | Lalpuria et al. |
| 8,339,586 | B2 | 12/2012 | Zahniser |
| 8,383,043 | B2 | 2/2013 | Padmanabhan |
| 8,467,063 | B2 | 6/2013 | Wardlaw et al. |
| 8,472,693 | B2 | 6/2013 | Davis et al. |
| 8,570,370 | B2 | 10/2013 | McCollum et al. |
| 8,573,033 | B2 | 11/2013 | Larsen |
| 8,744,164 | B2 | 6/2014 | Ozinsky et al. |
| 8,753,890 | B2 | 6/2014 | Lalpuria et al. |
| 8,815,537 | B2 | 8/2014 | Winkelman et al. |
| 8,837,803 | B2 | 9/2014 | Wang et al. |
| 9,176,121 | B2 | 11/2015 | Winkelman et al. |
| 9,217,695 | B2 | 12/2015 | Winkelman et al. |
| 9,341,550 | B2 | 5/2016 | Takedo |
| 9,354,242 | B2 | 5/2016 | Crowther |
| 9,366,606 | B1 | 6/2016 | McPeak et al. |
| 9,494,570 | B2 | 11/2016 | Bransky |
| 9,759,657 | B2 | 9/2017 | Kiesel |
| 9,767,343 | B1 | 9/2017 | Jones |
| 10,203,275 | B2 | 2/2019 | Herzog |
| 10,267,722 | B2 | 4/2019 | Rousseau |
| 10,625,259 | B1 | 4/2020 | Jones |
| 11,047,845 | B1 | 6/2021 | Barry, Jr. et al. |
| 2002/0028471 | A1 | 3/2002 | Oberhardt |
| 2003/0133119 | A1 | 7/2003 | Bachur, Jr. |
| 2003/0159999 | A1 | 8/2003 | Oakey |
| 2004/0086427 | A1 | 5/2004 | Childers |
| 2004/0156746 | A1 | 8/2004 | Larsen |
| 2005/0003554 | A1 | 1/2005 | Brasseur |
| 2005/0005684 | A1 | 1/2005 | Chien |
| 2005/0186114 | A1 | 8/2005 | Reinhardt |
| 2006/0094109 | A1 | 5/2006 | Trainer |
| 2006/0240545 | A1 | 10/2006 | Tomida et al. |
| 2007/0076190 | A1 | 4/2007 | Nakaya |
| 2007/0166195 | A1 | 7/2007 | Padmanabhan |
| 2008/0014589 | A1 | 1/2008 | Link |
| 2009/0123337 | A1 | 5/2009 | Noda et al. |
| 2009/0215072 | A1 | 8/2009 | McDevitt et al. |
| 2009/0269799 | A1 | 10/2009 | Winkelman |
| 2011/0005932 | A1 | 1/2011 | Jovanovich |
| 2011/0027826 | A1 | 2/2011 | Fukuya et al. |
| 2011/0134803 | A1 | 7/2011 | Dalvi et al. |
| 2012/0169863 | A1 | 7/2012 | Bachelet |
| 2012/0176498 | A1 | 7/2012 | Haas et al. |
| 2013/0171044 | A1 | 7/2013 | Nikonorov et al. |
| 2013/0176551 | A1 | 7/2013 | Wardlaw et al. |
| 2013/0208972 | A1 | 8/2013 | Levine et al. |
| 2013/0273524 | A1 | 10/2013 | Ehrenkranz |
| 2014/0038230 | A1 | 2/2014 | Beck |
| 2014/0147837 | A1 | 5/2014 | Kimura et al. |
| 2014/0178858 | A1 | 6/2014 | Reinhardt |
| 2014/0270458 | A1 | 9/2014 | Smith et al. |
| 2014/0295441 | A1 | 10/2014 | Egan |
| 2014/0347459 | A1 | 11/2014 | Greenfield et al. |
| 2014/0347463 | A1 | 11/2014 | Lin |
| 2015/0024436 | A1 | 1/2015 | Eberhardt |
| 2015/0060303 | A1 | 3/2015 | Blohm |
| 2015/0037806 | A1 | 5/2015 | Pollak |
| 2015/0192518 | A1 | 7/2015 | Baxter |
| 2015/0219544 | A1 | 8/2015 | Liu |
| 2015/0316477 | A1 | 11/2015 | Pollack et al. |
| 2016/0003718 | A1 | 1/2016 | Ikushima |
| 2016/0011221 | A1 | 1/2016 | Hegedus |
| 2016/0026852 | A1 | 1/2016 | Zahnizer et al. |
| 2016/0208306 | A1 | 7/2016 | Pollak et al. |
| 2016/0209320 | A1 | 7/2016 | Winkelman et al. |
| 2016/0246046 | A1 | 8/2016 | Yorav et al. |
| 2016/0279633 | A1 | 9/2016 | Bachelet et al. |
| 2017/0059459 | A1 | 3/2017 | McPeak et al. |
| 2017/0059590 | A1 | 3/2017 | McPeak et al. |
| 2017/0114386 | A1 | 4/2017 | McPeak et al. |
| 2017/0131303 | A1 | 5/2017 | Reinhardt |
| 2018/0106782 | A1 | 4/2018 | Pruitt |

FOREIGN PATENT DOCUMENTS

| | | |
|---|---|---|
| WO | WO2002089670 | 11/2002 |
| WO | 2004045770 | 6/2004 |
| WO | WO2005114144 | 1/2005 |
| WO | 2006113727 | 10/2006 |
| WO | 2007005907 | 1/2007 |
| WO | WO2012019118 | 9/2012 |
| WO | WO2014099629 | 6/2014 |

(56) References Cited

FOREIGN PATENT DOCUMENTS

| | | |
|---|---|---|
| WO | WO2014159692 | 10/2014 |
| WO | 2015173774 | 11/2015 |
| WO | WO2016051272 | 7/2016 |

OTHER PUBLICATIONS

Countess™ Automated Cell Counter, Invitrogen, User Manual, Rev. Date: Sep. 15, 2009.
Japanese Pat. Apl. No. 2019-520938, Office Action, dated Sep. 2021.
Search report and Opinion, PCTUS2017041274, dated Nov. 30, 2017.
Ben-Yosef Y. et al., "The HemoScreen, a novel haematology analyser for the point of care." J Clin Pathol. 2016, Jan. 19, 2016, p. 1-6.
HemoCue WBC System product informational brochure, HemoCue America, 2013.
"Comparison of image-based cell counting methods: Countess Automated Cell Counter vs. the hemocytometer", Invitrogen 2009, pp. 1-4.
U.S. Appl. No. 14/947,971; Office action dated Feb. 20, 2018.
U.S. Appl. No. 15/221,285; Office action dated Sep. 7, 2016.
U.S. Appl. No. 15/221,285; Amendment dated Dec. 7, 2016.
U.S. Appl. No. 15/221,285; Office action dated Jan. 13, 2017.
U.S. Appl. No. 15/221,285; Amendment dated Mar. 13, 2017.
U.S. Appl. No. 15/221,285; Amendment dated May 19, 2017.
U.S. Appl. No. 15/221,285; Notice of Allowance dated Jun. 2, 2017.
U.S. Appl. No. 15/221,285; Notice of Allowance dated Jun. 28, 2017.
U.S. Appl. No. 16/803,897; Office Action; dated Sep. 23, 2021.
U.S. Appl. No. 16/803,897; Amenment; dated Dec. 23, 2021.
U.S. Appl. No. 16/803,897; Office Action; dated Feb. 16, 2022.
U.S. Appl. No. 14/947,971; Amendment, dated Jul. 19, 2018.
U.S. Appl. No. 14/947,971; Office Action, dated Dec. 6, 2018.
U.S. Appl. No. 15/616,327; Office Action, dated Feb. 28, 2019.
U.S. Appl. No. 15/616,327; Amendment, dated Jun. 28, 2019.
U.S. Appl. No. 15/616,327; Office Action, dated Jul. 26, 2019.
U.S. Appl. No. 15/616,327; Amendment, dated Oct. 28, 2019.
U.S. Appl. No. 15/616,327; Notice of Allowance, dated Dec. 11, 2019.
U.S. Appl. No. 16/192,182; Office Action, dated Aug. 23, 2019.
U.S. Appl. No. 16/192,182; Amendment, dated Feb. 21, 2020.
U.S. Appl. No. 16/192,182; Office Action, dated Apr. 4, 2020.
U.S. Appl. No. 16/192,182; Amendment, dated Jul. 15, 2020.
U.S. Appl. No. 16/192,182; Notice of Allowance, dated Aug. 3, 2020.
U.S. Appl. No. 16/434,067; Office Action, dated May 25, 2021.
U.S. Appl. No. 16/803,897; Amendment, dated Dec. 23, 2021.
Japanese Pat. Apl. No. JP2019520938; Written Amendment, dated Feb. 28, 2022.
Japanese Pat. Apl. No. JP2019520938; Written Opinion, dated Feb. 28, 2022.
Japanese Pat. Apl. No. JP2019520938; Notice of Reasons for Refusal, dated Jan. 9, 2022.
European Pat. Apl. No. EP3482189; Amendment, dated Jan. 21, 2022.
European Pat. Apl. No. EP3482189; Office Action, dated Sep. 22, 2021.
European Pat. Apl. No. EP3482189; Amendment, dated May 14, 2021.
European Pat. Apl. No. EP3482189; Office Action, dated Jul. 4, 2021.
European Pat. Apl. No. EP3482189; Amendment, dated Feb. 2, 2020.
European Pat. Apl. No. EP3482189; Supplementary European search report, dated Jul. 17, 2020.
U.S. Appl. No. 15/017,498; Requirement for Restriction/Election, dated Apr. 17, 2018.
U.S. Appl. No. 15/017,498; Reply, dated Apr. 26, 2018.
U.S. Appl. No. 15/017,498; Office Action, dated Jul. 31, 2018.
U.S. Appl. No. 15/017,498; Reply, dated Oct. 31, 2018.
U.S. Appl. No. 15/017,498; Office Action, dated Jan. 31, 2019.
U.S. Appl. No. 15/017,498; Amendment, dated Jun. 28, 2019.
U.S. Appl. No. 15/017,498; Office Action, dated Jul. 12, 2019.
U.S. Appl. No. 15/017,498; Amendment, dated Jul. 17, 2019.
U.S. Appl. No. 15/017,498; Office Action, dated Jul. 29, 2019.
U.S. Appl. No. 15/017,498; Amendment, dated Jul. 31, 2019.
U.S. Appl. No. 15/017,498; Office Action, dated Aug. 21, 2019.
U.S. Appl. No. 15/017,498; Amendment, dated Oct. 19, 2019.
U.S. Appl. No. 15/017,498; Office Action, dated Jan. 23, 2019.
U.S. Appl. No. 15/017,498; Amendment, dated Jun. 23, 2020.
U.S. Appl. No. 15/017,498; Amendment, dated Jul. 15, 2020.
U.S. Appl. No. 15/017,498; Amendment, dated Oct. 21, 2020.
U.S. Appl. No. 15/017,498; Office Action, dated Dec. 17, 2020.
U.S. Appl. No. 15/017,498; Amendment, dated Jun. 16, 2021.
U.S. Appl. No. 15/017,498; Office Action, dated Sep. 23, 2021.
U.S. Appl. No. 15/017,498; Amendment, dated Nov. 23, 2021.
U.S. Appl. No. 15/017,498; Notice of Allowance, dated Jan. 10, 2022.
Natasha S. Barteneva et al, Imaging flow Cytometry: Coping with Heterogeneity in Biological Systems, Journal of Histochemistry & Cytochemistry, 2012, 11 pg(s) (Year: 2012).
Ingrid Schmid, Flow Cytometry Recent Perspectives, Intech, www.intechopen.com, Jun. 13, 2012, pp. 11-203, 219, 385 (Year: 2012).
Keisuke Goda, High-throughput single-microparticle imaging flow analyzer, Harvard University, Mar. 22, 2012, 6 pages (Year: 2012).
Bong-Hyun Jun, Multilayer fluorescene optically encoded beads for protein detection, Elsevier, Mar. 9, 2009, 3 pgs (Year: 2009).
Howard M. Shapiro, 'Personal Cytometers: Slow Flow or No Flow?, International Society for Analytical Cytology, Nov. 23, 2005, Cytometry Part A 69A: 620-630 pgs (Year: 2005).
Chiristian K. Sieracki et al., An imaging-in-flow system for automated analysis of marine microplankton, Marine Ecology Prog Ser vol. 168; 285-296, Jul. 9, 1998 (Year: 1998).
P. Schlenke et al., Evaluation of a Flow Cytometric Method for Simultaneous Leukocyte Phenotyping and Quantification by Fluorescent Microsheres, Wiley-Liss Inc, May 27, 1998, vol. 33: 310-317 pgs (Year 1998).
Huang et al., "Development of a Flow Cytometry Based Miniature Chemical Fluid Analysis System Using Fluorescent Microbeads", SPIE Biomedical Optics, BIOS 97, conference proceeding, 1997, 9 pgs, (Year: 1997).
Winkelman, et al. "A Novel Automated Slide-Based Technology for Visualization, Counting, and Characterization of the Formed Elements of Blood," Arch Pathol Lab Med. Aug. 2017, p. 1107-1112.
U.S. Appl. No. 14/947,971; Reply, dated Oct. 12, 2017.
U.S. Appl. No. 14/947,971; Requirement for Restriction/Election, dated Jul. 12, 2017.
U.S. Appl. No. 16/235,099; Amendment, dated Jun. 15, 2022.

* cited by examiner

AUTOMATED MICROSCOPIC CELL ANALYSIS

CROSS-REFERENCE TO RELATED APPLICATION

This application claims priority to U.S. application Ser. No. 14/947,971, filed Nov. 20, 2015, and to U.S. provisional applications Nos. 62/138,359, filed Mar. 25, 2015, 62/113,360 filed Feb. 6, 2015, and 62/084,760, filed Nov. 26, 2014, which are all herein incorporated by reference.

FIELD OF THE INVENTION

This invention pertains to analyzers and methods for automatically performing microscopic cell analysis tasks, such as counting blood cells in biological samples.

BACKGROUND OF THE INVENTION

There are a variety of methods for enumerating particles, such as cells, in biological samples. The most rudimentary method consists of a hemocytometer and a microscope. A hemocytometer is a precision slide device where biological samples are introduced into a chamber by capillary action or by pipette with ruled square markings, such as 1×1 mm squares, and a known depth. These known dimensions are used to compute a unit volume, typically 0.01 uL, so that the concentration of cells can be accurately determined. Modern methods, such as impedancemetry (Coulter principle U.S. Pat. No. 2,656,508) and flow cytometry are more commonly used today for rapid cell counting, sizing, and classification, for diagnostic tests such as the Complete Blood Count (CBC).

These prior art approaches are used in thousands of tests per day, yet the existing methods have shortcomings. The hemocytometer with microscope method can be extremely time-consuming and require skilled technicians. It can also be operator-dependent, and is susceptible to interpretative discrepancies. The number of cells in each square is relatively small, which can result in unreliable cell counts with high standard deviations. Impedancemetry and flow cytometry are broadly used in today's laboratories for higher throughput, but again still require skilled operators for use and maintenance of the instruments and interpretation of the results.

SUMMARY OF THE INVENTION

This invention comprises a method for performing a complete blood count (CBC) on a sample of whole blood taken from a patient, by a finger stick, heel stick, or intravenously, performed by metering a predetermined amount of the whole blood and mixing it with a predetermined amount of diluent and stain and transferring a portion thereof to an imaging chamber of fixed dimensions and utilizing an automated microscope with digital camera and cell counting and recognition software to count every white blood cell and red blood corpuscle (referred collectively as cells throughout this publication for shorthand), and platelet in the sample diluent/stain mixture to determine the number of red cells, white cells, and platelets per unit volume, and analyzing the white cells with cell recognition software to classify them. The CBC can also be performed by metering a predetermined amount of whole blood and mixing it with an undetermined amount of diluent and stain and transferring the entire mixture to an imaging chamber and counting every white cell, red cell, and platelet, to determine the number of red cells, white cells, and platelets per unit volume and analyzing the white cells with cell recognition software to classify them, as more fully explained below. The CBC can also be performed by counting only a sampling of cells that are statistically significant to determine cell concentrations from the aforementioned two methods. A detailed description of these methods together with apparatuses for carrying out the processes are set forth below.

In one aspect, the invention features, a single-use test cartridge for use with an analyzer that includes an automated microscope for analyzing cells in a biological sample. The test cartridge includes a body that defines: 1) a sample collection port and a input channel for receiving the sample from a venipuncture or capillary sample; 2) a rotary valve having a pass-through conduit for metering a predetermined volume of sample, and which is fluidically coupled to the sample collection port and input channel when the valve is in a first flow position; 3) a vacuum channel for conveying a negative pressure relative to the pressure at the sample collection port and which is also fluidically coupled to the pass-through conduit when the valve is in its first flow position; 4) a diluent channel for conveying diluent and which is fluidically coupled to the pass-through conduit when the valve is in a second flow position; 5) a mixing chamber that is also fluidically coupled to the pass-through conduit when the valve is in the second flow position; 6) an imaging chamber fluidically coupled to the pass-through conduit when the valve is in a third flow position; and 7) a connecting channel fluidically coupled to the pass-through conduit and to the mixing chamber when the valve is in the third flow position. The test cartridge is constructed and adapted to allow the sample to flow from the sample collection port and input channel, through the pass-through conduit of the valve, and into the vacuum channel when the valve is in its first flow position; to allow diluent and sample to flow through the pass-through conduit and into the mixing chamber when the valve is in its second flow position; and to allow the mixture of sample and diluent to flow through the connecting channel and the pass-through conduit into the imaging chamber when the valve is in its third flow position. The test cartridge can contain a vent or a plurality of vents to allow portions of the sample, diluent, and mixture of sample and diluent to be moved pneumatically in the test cartridge, as is more fully explained below. Some of these vents may be constructed with a hydrophobic material, such as micro porous Teflon, to permit the flow of air and not fluids.

The body of the test cartridge can further define a photometric chamber, which is fluidically coupled to the sample collection port and input channel, for measuring the concentration of an analyte, such as hemoglobin, in the sample. The body of the cartridge can further define at least one diluent port fluidically coupled to the diluent channel for connection to a diluent reagent supply. The body of the cartridge can further define at least one vacuum port connected to the vacuum channel for connection to a vacuum supply. The mixing chamber can also be fluidically coupled through a direct channel to the imaging chamber instead of being fluidically coupled through the connecting channel and the pass-through conduit. In this case, a second vacuum port can be connected to the imaging chamber, with some of the mixture in the mixing chamber being pulled into the imaging chamber through the direct channel by a vacuum supply applied to the second vacuum port. The test cartridge can include a magnetic mixing bead or bar in the mixing chamber, which can be activated by a mixer actuator when the test cartridge is inserted into the analyzer for receiving the test cartridge, as more fully described below. Other approaches to mixing could be used, such as ones including the application of ultrasonic energy, pulsing the fluid using the vacuum pump, bubble mixing, vibration, rocking, or even forcing fluids through a variegated channel on the cartridge (passive mixing). The mixing preferably takes place in a separate mixing chamber, but it can also take place in the imaging chamber if the chamber and the diluent channel are fluidically coupled to the pass-through conduit in the valve, in which case a separate mixing chamber would be unnecessary.

The test cartridge can be made out of glass or optically clear plastic, such as acrylic, polystyrene, polycarbonate, or cyclic olefin polymers (COP or COC), to allow process monitoring of the fluids, as explained below. The surfaces, channels, and chambers of the test cartridges may be coated with an anti-coagulant, such as EDTA, or a hydrophilic coating to help the fluids move throughout the cartridge and to minimize bubbles. The test cartridge can be shaped like a microscope slide as illustrated in the various embodiments of the test cartridge. Alternate shapes for the test cartridge such as circular or polygonal may also be devised. In one embodiment, a pump can be fluidically coupled to the sample collection port to aspirate a sample from a finger stick or capillary tube. The pump can comprise a mechanism for moving small volumes fluid such as a flexible bulb. Alternatively, the sample collection port can be dimensioned to draw the sample into the input channel and photometric chamber by capillary action. The cartridge can also be designed to hold a vacuum for drawing the sample through the cartridge. The test cartridge can be preloaded with diluent and one or more stains including a fluorescent stain and/or a mixture of diluent and stain.

The analyzer can include a photometer that aligns with the photometric chamber in the test cartridge to perform photometric measurements of the sample in the photometric chamber. This photometer could be an absorbance, extinction, or reflective measurement. The analyzer can include a machine-readable depth indicator for measuring the depth of the photometric chamber and the imaging chamber. The analyzer can include actuators to dispense diluent, stain, or a mixture of diluent and stain, preloaded on the test cartridge, to the diluent channel and provide vacuum to the vacuum channel or imaging chamber on the test cartridge. The analyzer can include a process monitoring camera positioned to acquire digital images of the fluids in the cartridge. The analyzer can further include fluid monitoring logic to automatically control and monitor operation of the fluids in the test cartridge utilizing information from the process monitoring camera. Output from the fluid monitoring logic can be operatively connected to the process monitoring logic to control the movements of fluids in the test cartridge by activating an actuator that positions the rotary valve to various flow positions and by the dispensing of diluent-stain to the diluent channel and by providing a negative pressure to the vacuum channel and/or imaging chamber of the test cartridge. The fluid monitoring may also be done by a plurality of optical, conductive, or capacitive sensors that are triggered by fluid at particular positions throughout the cartridge.

The analyzer can include a mixer actuator for activating the mixing bead or bar in the mixing chamber, a photometric detector positioned to acquire readings from the photometric chamber on the test cartridge, and an automated microscope positioned to acquire digital images of the cells and platelets in the imaging chamber. The analyzer includes cell analysis logic to perform analysis of acquired images of the cells in the imaging chamber. The cell analysis logic also includes cell characterization logic, for classifying the normal and abnormal cells, and cell counting logic to count the red cells, white cells, and platelets. The automated microscope can be operative to acquire bright-field images, or both bright-field and fluorescent images. The analyzer can further include a digital network communications interface.

In one embodiment of the present invention, the test cartridge is not preloaded with diluent or stain. Instead, the analyzer includes a removable reagent supply module. The reagent supply module includes a cradle for interfacing with the test cartridge, a vessel for holding a diluent and at least one stain, a diluent metering pump fluidically coupled to the vessel, and a diluent output port fluidically coupled to the metering pump and constructed to fluidically interface with the diluent port and channel of the test cartridge when the cartridge is in the cradle. The metering pump can drive metered diluent-stain through the diluent channel and, together with the sample, through the pass-through conduit of the valve into the mixing chamber, when the valve is in the second flow position. Alternatively, the diluent metering pump may be part of the analyzer and the reagent supply module is used only to supply the diluent.

In one embodiment the size of the vessel is of sufficient capacity to provide diluent-stain to dilute several samples with a diluent-stain to sample ratio of 10:1 to about 250:1. The reagent supply module can include a self-priming mechanism for priming the diluent-stain and for eliminating air bubbles. In such an embodiment, the reagent supply module may also include a vacuum chamber and vacuum port which interfaces with, and is connected to, the vacuum ports of the test cartridge when the cartridge is in the cradle to provide a vacuum to the vacuum channel or imaging chamber. The reagent supply module may further include a chamber for collecting waste diluent-stain from the priming process as explained below.

Systems according to the invention can exhibit better quantitative accuracy than manual microscope analyses, which tend to be limited by variability in sample preparation and limited counting statistics. In the present invention, sample preparation is improved by removing critical operator fluid handling steps and by automation of all dilution steps. A complete set of system controls can be incorporated to ensure that sample dilutions are accurate and repeatable. This can be particularly important in laboratories where metrology standards are not universally followed and skill level is low. Where every cell and platelet is counted in the entire mixture of a predetermined amount of sample and diluent-stain, any error in the sample dilution process will not affect the cell count concentration. Similarly, any error in the dimensions of the imaging chamber in the manufacturing process will not affect the cell count concentrations.

Systems according to the invention can also save time that would otherwise be allocated to manual hemocytometer slide preparation, setup time, and microscope focusing, which can limit the volume of blood samples that can be analyzed. Automation can greatly increase the rate of image acquisition and analysis allowing for more cells to be analyzed and counted. This can improve the counting statistics and overall precision of the system.

Systems according to the invention can also extend the capabilities of cell counting methods by enabling CBC point-of-care testing, i.e. near patient testing, to permit immediate clinical decisions to be made. The systems can be designed to be run with little operator involvement and by personnel having a relatively low skill level.

They also can be engineered to be inexpensively manufactured and easily serviced, allowing them to be more readily deployed at point-of-care sites, such as at the patient's bedside and in physician's offices and at emergency sites.

DESCRIPTION OF AN ILLUSTRATIVE EMBODIMENT

Figure 1B:
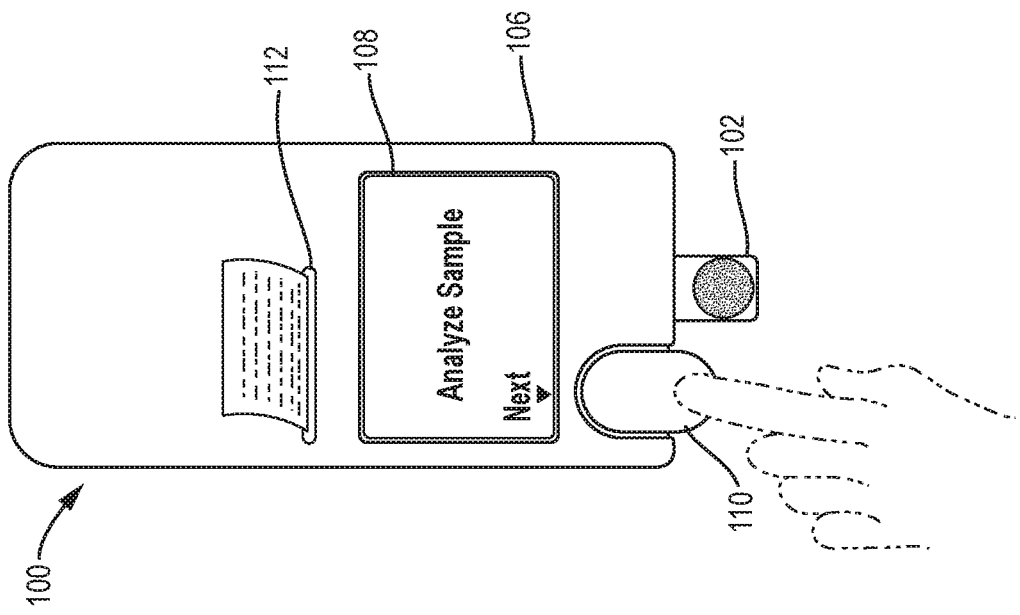
FIG. 1B is an elevation view diagram of the cell analyzer showing the initialization of a test for the inserted cartridge.
Figure 1A:
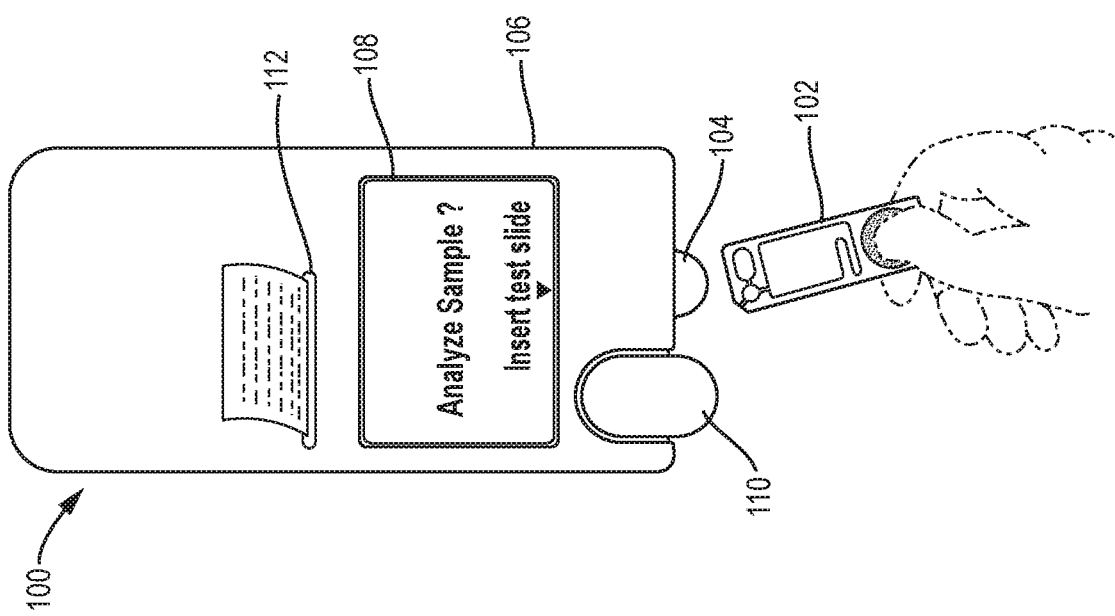
FIG. 1A is an elevation view diagram of an illustrative cell analyzer according to the invention, showing a cartridge being inserted into the analyzer.
Figure 2A:
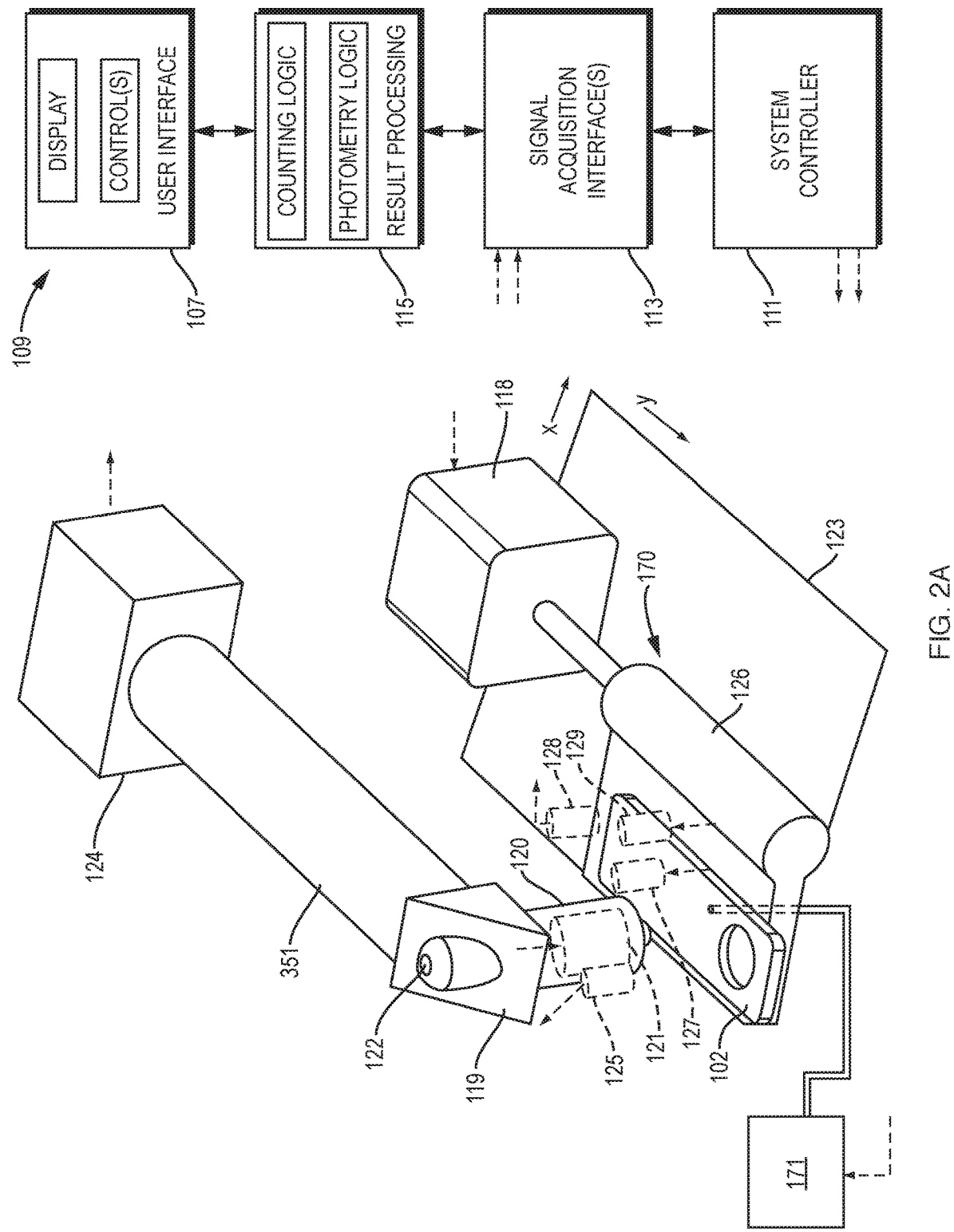
FIG. 2A is a diagrammatic view showing a breakdown of the analyzer and test cartridge.

Referring to FIGS. 1A, 1B, and 2A, an illustrative cell analyzer 100, according to the invention, includes a housing 106 that supports a removable reagent supply module 170 with a cradle 104 into which a test cartridge 102 can be inserted. The housing also supports a "go" button 110, a display screen 108, and a printer 112. Other configurations of the analyzer are of course possible without departing from the invention. The "go" button's function could be triggered by insertion of the test cartridge or be provided through soft prompting on a touchscreen instead of through the use of a discrete button. The printer could be housed separately from the analyzer. And while the cartridges may shaped like microscope slides, a working system could be built around cartridges dimensioned in a variety of other shapes and sizes.

In operation, a technician or other operator first collects a sample, such as a blood sample from a patient finger stick, heel stick, or by venipuncture in the test cartridge 102. He or she then introduces the cartridge into the cradle 104 of a reagent supply module, and presses the "go" button 110. Where patient samples are collected in a capillary tube, the test cartridge can be inserted in the cradle first and the capillary tube can be inserted into a collection port dimensioned to receive capillary tubes. The analyzer then analyses the sample, as will be discussed in more detail below, and displays and/or prints the results. These results can include test results, error messages, or further instructions, such as instructions to manually review results or repeat the test.

Figure 6:
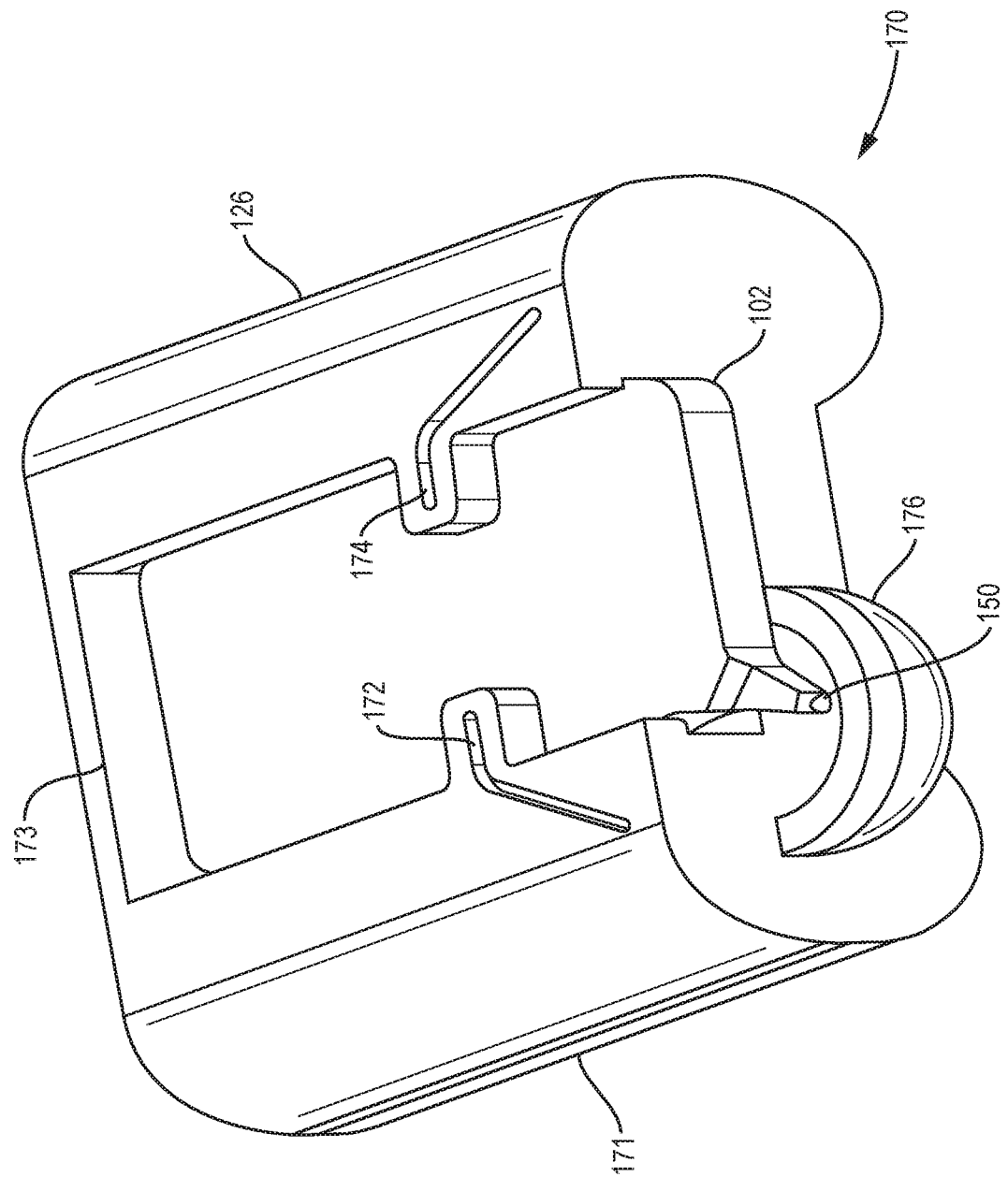
FIG. 6 is a perspective view of an illustrative reagent supply module for the analyzer of FIG. 1A, and showing a test cartridge inserted in the module.

Referring also to FIGS. 1A, 2A, and 6, the analyzer housing 106 holds an automated microscope assembly 351 and a removable reagent supply module 170 containing a cradle 104 for receiving the test cartridge 102. The microscope assembly includes an objective lens 120 with a focusing mechanism 121 and an X-Y stage 123 for positioning the test cartridge 102, while it is held in place in the cradle, relative to the objective lens 120. A digital camera 124 is positioned to receive images from the microscope, and a light source, such as a light emitting diode (LED) 122, can be included to provide illumination for florescence measurements. The reagent supply module includes a diluent metering pump 126, such as a syringe pump that includes a piston that slides within a cylinder driven by a linear stepper motor 118. The reagent supply module also includes a vacuum pump 171 for pulling fluids through channels as needed. The analyzer 100 includes an electronic subsystem 109 FIG. 2B, which directs movements of fluids throughout the cartridge 102, captures images, takes photometric measurements, and performs image processing functions, all of which is more fully described below.

The X-Y stage 123 may comprise stepper motors, a drive train, and a positional feedback control mechanism (not shown) known to those skilled in the arts. The X-Y stage 123 is used to position the test cartridge relative to the objective lens for the purposes of collecting images of cells and to the photometer for the purpose of taking photometric measurements. It is also used to position the test cartridge so that the digital camera may be used to control the positioning of fluids and the detection of interferences in the fluids, such as air bubbles or clots. It will be understood that in an alternative embodiment, an X-Y stage mechanism similar to X-Y stage 123, could move the objective lens 120 and digital camera 124 relative to the test cartridge. Alternatively, the stage could be rotational utilizing polar coordinates or any other two-dimensional movement to image the slide.

The objective lens 120 and focusing mechanism 121 are chosen for the types of cells to be viewed and counted. Positional accuracy of the focusing mechanism 121 should be optimized for the depth of focus of the objective lens 120. The depth of focus is determined by the magnification and numerical aperture (NA) of the objective. For example, a 10×/0.25 NA objective may only need positional accuracy of 5 um, but a 40×/0.65 NA may need positional accuracy of less than 1 um. The smallest sized features that need to be resolved for the cells to be analyzed determine the characteristics of the objective lens 120. The smallest sized cells in a CBC are the platelets. For example, a 0.1 NA may be used to count RBC and WBC, but a 0.4 NA may be needed to count platelets and to differentiate the WBC into the different subpopulations, such as lymphocytes, monocytes, neutrophils, eosinophils, basophils, and abnormal WBC. A plurality of objective lenses may be used to achieve a faster scan by first counting the WBC and/or RBC with a low power lens, such as 4×/0.1NA and a higher powered lens, such as 20×/0.4NA to count platelets and determine the WBC differential on a subset of the sample.

The analyzer of the present invention uses both bright-field and fluorescence illumination. The bright-field illumination mode uses a white light source 127 to capture a broad spectrum of transmitted light from the sample. A color digital camera or a black-and-white digital camera may be used to collect these images. If a black-and-white camera is used, filters can be used to isolate particular wavelength bands of light. Alternatively, multiple wavelengths of illumination may be used to construct a composite image. Epi-fluorescent illumination is also incorporated to excite fluorophores that can be used in the assay. A dichroic mirror 119 is used to block the excitation wavelengths from saturating the digital camera while allowing the emission wavelengths to pass. Alternatively, a beam splitter and optical filters could be used to isolate various wavelengths of interest. The light source for the bright-field and fluorescent illuminations may be based on a halogen bulb, light emitting diode (LED), or any other suitable illumination technology. Multiple excitation wavelengths and emission filters may be used, if a plurality of fluorophores is desired or if a fluorophore has multiple emission wavelength bands.

The analyzer includes an illumination source 129 and corresponding photometric detector 128 to allow for the acquisition of photometric measurements on the sample in the photometric chamber, such as may be employed by those skilled in the art, to obtain a hemoglobin measurement.

The analyzer also includes an electronic subsystem 109 (FIG. 2B), which includes a system controller 111, a signal acquisition interface 113, a result processor 115, and a user interface 117. The system controller 111 provides control signals on control lines to various parts of the analyzer. Systems controller 111 is responsible for controlling the diluent metering pump 126, the vacuum pump 171, and positioning the rotary valve 134 on the test cartridge 102 for sequencing fluid movements on the test cartridge 102. The systems controller 111 can also be used to release a reagent on the test cartridge if the reagent is included in the cartridge. The systems controller 111 is also responsible for controlling the X-Y stage 123, the focusing mechanism 121, the photometric measurements, activating a mixing actuator 127, switching between bright field and fluorescent measurements, and turning the illumination sources 122 and 129 on and off.

The system controller can also perform other system functions, such as temperature control and various calibrations and system checks. The electronic subsystem includes one or more well-known hardware interface elements, such as analog to digital or digital to analog (ADC or DAC), which can be configured to produce a variety of different types of analog and/or digital signals and that are usable by the various parts of the electronic subsystem.

Figure 2B:
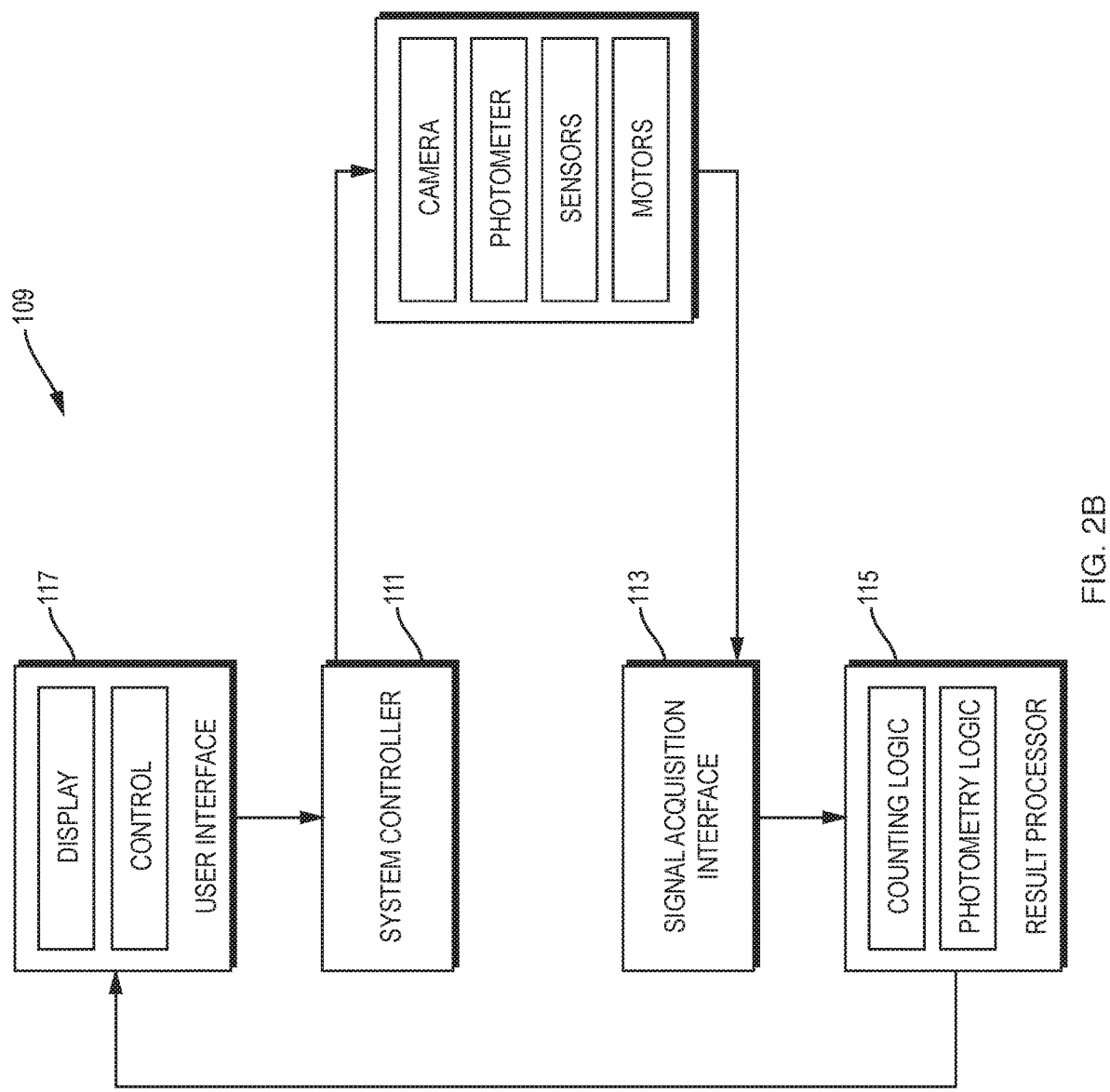
FIG. 2B illustrates the electronic subsystem.

The analyzer also includes a signal acquisition interface 113 that receives signals from different parts of the analyzer, as illustrated in FIG. 2B. It is responsible for receiving image data from the digital camera 124, for receiving light level signals from the photometric detector 128, and for receiving displacement signals from the machine-readable depth indicator 125. The signal acquisition interface can also receive other signals used by the analyzer, such as from limit and tamper switches. The signal acquisition interface includes one or more well-known hardware interface elements, such as ADC/DAC, which can be configured to control and receive a variety of different types of analog and/or digital signals and format them for use by the result processor 115 or other processing logic.

The result processor 115 automatically processes signal information received by the acquisition interface 113 to derive more clinically useful parameters. For example, the result processor 115 uses the digital images and photometric measurements to determine cell concentrations, cell differentiation, and hemoglobin concentration. It includes logic embodied in software or hardware to perform this processing, such as counting logic for counting cells and photometry logic for processing photometric results.

The analyzer also includes a user interface 117 that interfaces with the user, such as to receive inputs and report results. It can include a variety of different types of well known user interface elements, such as controls and displays, including the "go" button 110, the display screen 108, and the printer 112 shown in FIG. 1. It can also include electronic interfaces, such as Laboratory Information Systems (LIS) or network interface to communicate results to remote users or systems. The electronic interface may also be wireless by use of local area wireless computer networking (Wi-Fi) or Bluetooth communication protocols.

In one embodiment, the electronic subsystem 109 is based on a custom programmed microcontroller and suitable interface circuitry. In an alternate embodiment, electronic subsystem 109 could be based on a standard personal computer platform with a suitable input and output (I/O) module. Some or all of the electronic subsystem 109 could be implemented with dedicated circuitry as well.

The test cartridge 102 of the present invention consists of a sample collection mechanism, valve for metering the sample, fluidic connections, photometric chamber, mixing chamber, and imaging chamber. Three different examples of test cartridges are presented in this application.

Referring to FIGS. 1A, 3A, 6, and 12, one embodiment of a cartridge 102, shaped like a microscope slide, employs a flexible bulb 138 to draw a biological sample, such as blood, from a finger stick, into a sample collection port 130 and into an input channel 132 of the cartridge. From there it is drawn through a pass-through conduit 135 in a rotary valve 134, which is in a first flow-position, and also into a photometric chamber 136 (step 200 FIG. 12). Once the sample is aspirated, the cartridge can be inserted into the cradle 104 of the reagent supply module 170. A photometric measurement, such as a hemoglobin measurement, can be made on the blood sample in the photometric chamber 136 by utilizing the photometric detector 128 and illumination source 129 in the analyzer (FIG. 2).

Figure 3A:
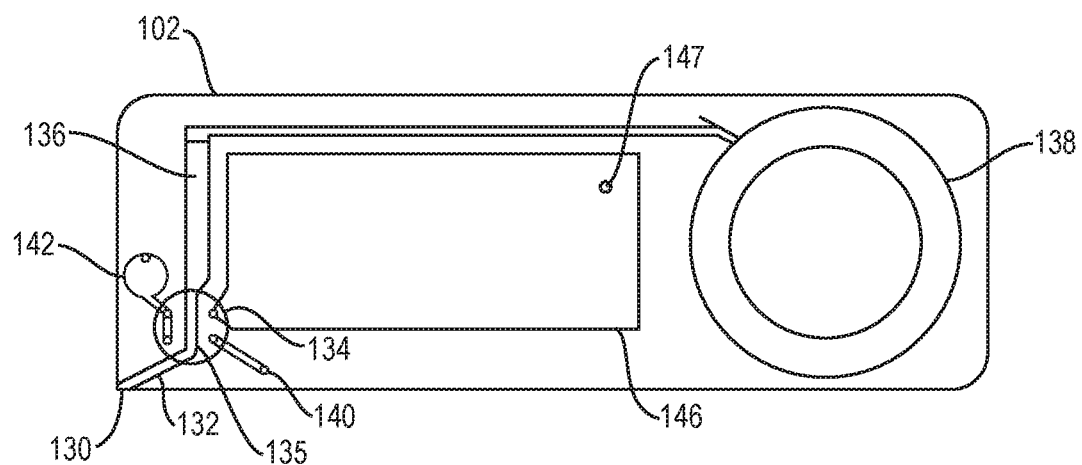
FIG. 3A is a plan view of an illustrative test cartridge with pump aspirator and shown with rotary valve in first flow position.
Figure 3B:
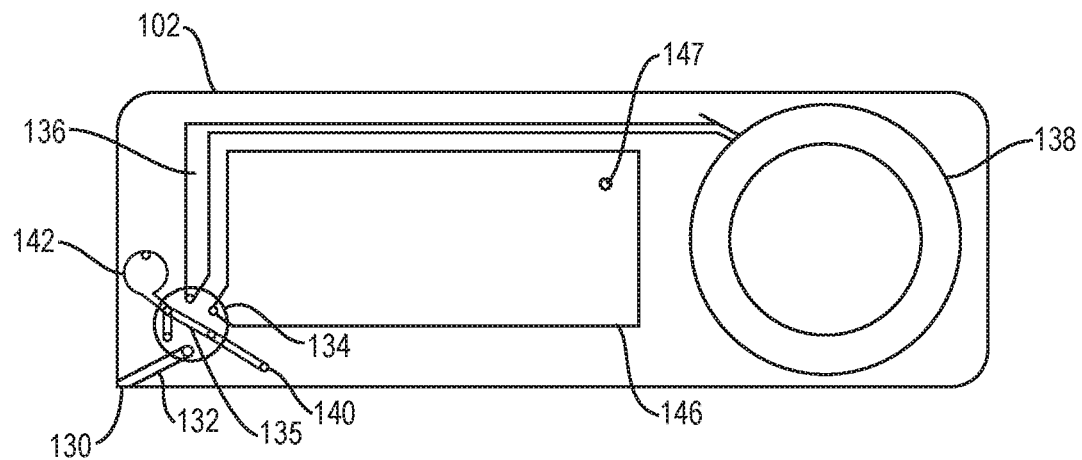
FIG. 3B is a plan view of the cartridge of FIG. 3A, shown with valve in second flow position.

Referring to FIG. 3B, the analyzer, through the use of an actuator (not shown), rotates the valve 134 to a second flow position. This rotation traps a predetermined amount of blood in the pass-through conduit 135 in the valve effectively causing it to act as a metering chamber (step 208). With the valve in the second flow position, the metered blood sample can be pushed by a flow of diluent-stain from a diluent channel 140, connected to a diluent metering pump 126 (FIG. 2), into a mixing chamber 142 (step 212). The diluent-stain and metered blood sample are mixed in the mixing chamber 142 (step 214) by the mixing actuator 127 (FIG. 2.

Figure 3C:
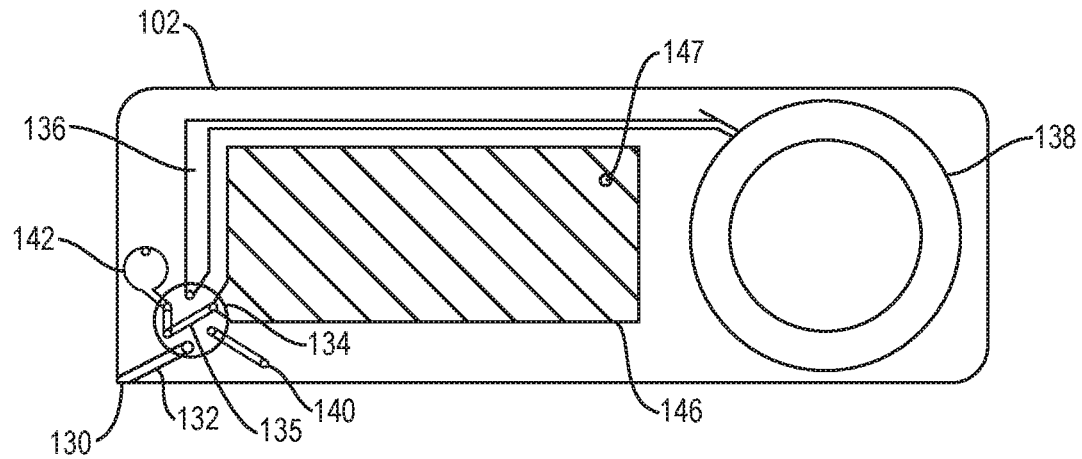
FIG. 3C is a plan view of the cartridge of FIG. 3A, shown with valve in third flow position.

Referring to FIG. 3C, the rotary valve 134 is shown in a third flow position wherein the mixing chamber is coupled fluidically with a connecting channel 131 and the pass-through conduit 135, and with the imaging chamber 146. This allows the mixture of diluent-stain and blood to be transferred to the imaging chamber 146 in the cartridge 102 (step 216) by applying a vacuum to the vacuum port 147 of the imaging chamber 146, which is connected to the vacuum pump 171 (FIGS. 2, 6). The imaging chamber should have a depth large enough so that the cells can pass into the imaging chamber and small enough to prevent the cells from overlapping or clumping when the cells settle to the bottom of the imaging chamber. This depth is preferably between around 10 um and 200 um. In one embodiment, the depth is about 100 um and the ratio of diluent-stain to the metered volume of the sample is 40 to 1. The automated microscope can then obtain one or more images of the blood cells and platelets, including bright-field and fluorescent images (step 218). The obtained images of the cells and platelets are then analyzed (step 220), as more fully explained below.

The analyzer determines if the results fall inside one or more predetermined ranges (step 230). If they do, they are reported as normal (step 232). If not, they are reported as anomalous (step 234). A report of anomalous results could arise out of a variety of conditions, such as a contaminated sample or a blood count that is associated with an unusual patient condition.

Figure 4A:
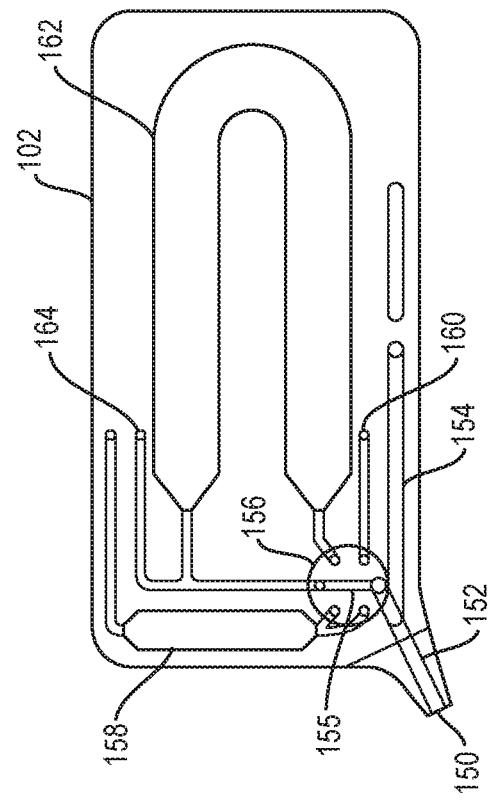
FIG. 4A is a plan view of an illustrative capillary draw test cartridge shown with sample aspirated.

Referring to FIG. 4A, a second type of test cartridge 102 employs capillary action to draw a biological sample such as blood that includes cells and platelets into a sample collection port 150 and into input channel 152 fluidically connected to a rotary valve 156 and photometric chamber 154. The photometric chamber is vented and designed to fill itself from the input channel by capillary action. The depth of the photometric chamber should be preferably between around 50 and 1000 um to allow for absorbance and/or reflectance measurement of the sample. In one embodiment, it is around 50-200 um in depth. During a photometric measurement, the valve remains fixed in its initial position as illustrated in FIG. 4A where the pass through conduit 155 is not fluidically coupled with any channel or chamber in the cartridge.

Figure 4B:
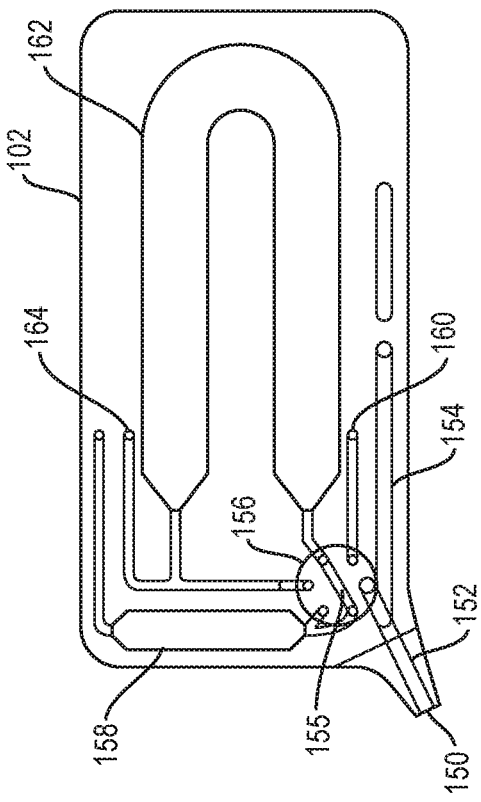
FIG. 4B is a plan view of the cartridge of FIG. 4A, with rotary valve in first flow position.

Referring to FIG. 4B, rotary valve 156 is shown positioned in a first flow position wherein the pass-through conduit 155 is fluidically coupled with the input channel 152 and vacuum channel 161 and vacuum port 164. When rotary valve 156 is in this first flow position, the sample may be drawn through the pass-through conduit 155 and into vacuum channel 161 by suction from the vacuum pump 171 (FIG. 2), which is connected to vacuum port 164. Alternatively, the sample could be pushed into the pass-through conduit 155 by use of a positive-pressure pump. The amount of sample drawn into the vacuum channel should be sufficient to minimize the risk of contamination, such as by interstitial fluids from a whole blood finger stick, for that portion of the sample remaining in the pass-through conduit 155.

Figure 4C:
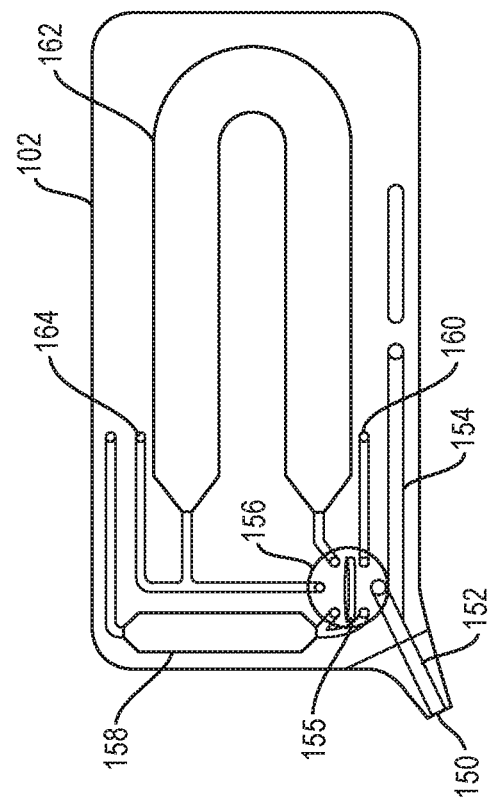
FIG. 4C is a plan view of the cartridge of FIG. 4A, with rotary valve in second flow position.

Referring to FIG. 4C, rotary valve 156 is in a second flow position. Rotating to this position after the sample has been drawn through pass-through conduit 155 traps a predetermined amount of blood in the pass-through conduit 155, effectively causing it to act as a metering chamber. The metered blood sample can then be pushed by a flow of diluent-stain from a diluent input port 160 connected to a diluent metering pump 126 (FIG. 2) into a vented mixing chamber 158. The diluent-stain and metered blood sample are then mixed in the mixing chamber by a mixing actuator 127 (FIG. 2).

Figure 4D:
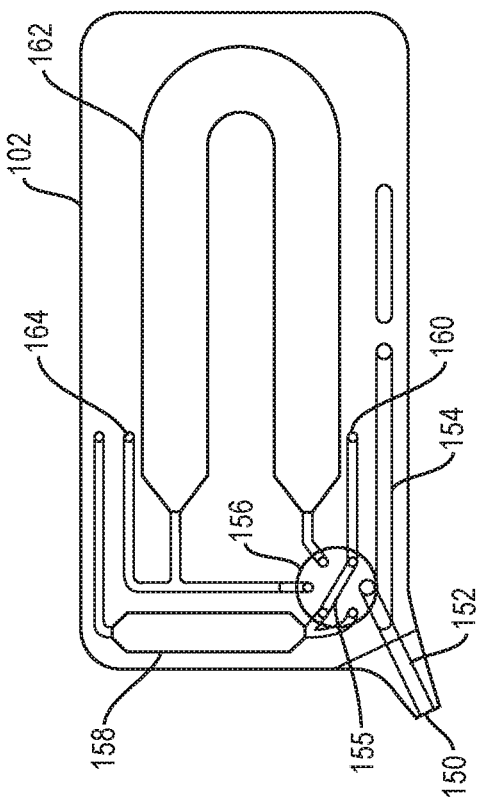
FIG. 4D is a plan view of the cartridge of FIG. 4A, with the rotary valve in third flow position.

Referring to FIG. 4D, rotary valve 156 is shown positioned in a third flow position wherein the mixing chamber 158 is fluidically coupled by connector channel 131 and pass-through conduit 155 to the imaging chamber 162. In this position, the mixture of blood and diluent-stain, or a portion thereof, as is more fully set forth below, can be pulled into the imaging chamber 162 by suction provided through the vacuum port 164 connected to vacuum pump 171 (FIG. 2). Alternatively, the mixture of blood and diluent-stain could be pushed into the imaging chamber by use of a positive-pressure pump. The mixing chamber could also be fluidically coupled directly to the imaging chamber through a channel instead of through the pass-through conduit 155 in rotary valve 156. The automated microscope can then image the blood cells and platelets in the imaging chamber 162. A photometric measurement, such as a hemoglobin measurement, can be performed on the sample in the photometric chamber 154, if it has not already been performed. It is also possible to make a photometric measurement on the sample after dilution in the imaging chamber 162.

The present invention utilizes a movable valve to sequence fluid movements on the test cartridge 102. In one embodiment the movable valve also comprises a metering channel of predetermined volume such that the valve can both direct and meter the flow of fluids. FIG. 5A illustrates the valve stem 144 of a face valve, which maybe incorporated into rotary valve 134 (FIG. 3A). Valve stem 144 includes a metering channel 135 having a predetermined volume, which may be used to meter the sample in the present invention.

Figure 5B:
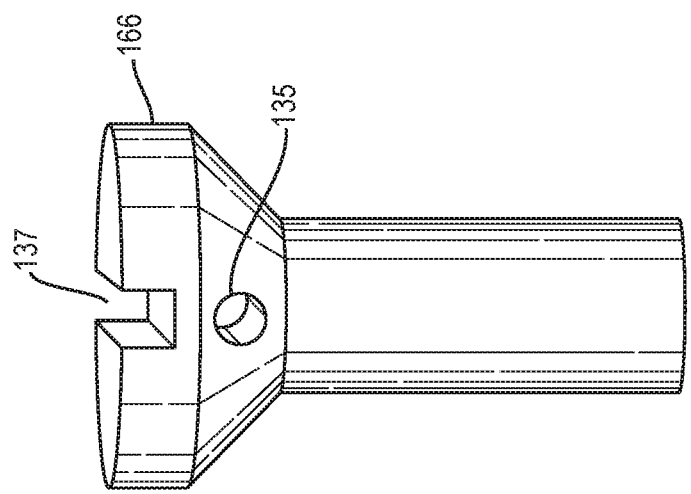
FIG. 5B is a side view of a valve stem with a though-hole pass-through conduit for a test cartridge.
Figure 5A:
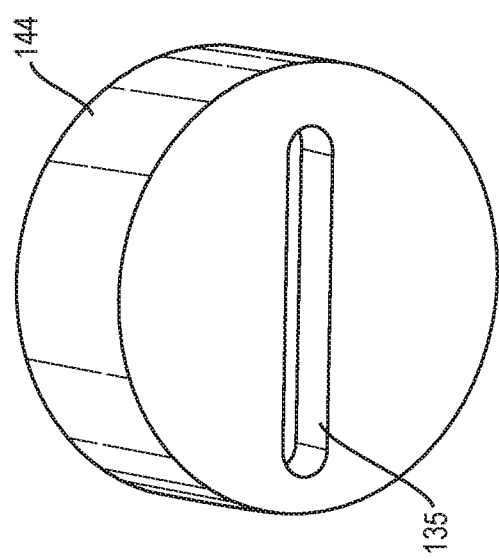
FIG. 5A is a perspective bottom view of a pass-through conduit in a face of a valve stem for a test cartridge.

FIG. 5B illustrates the valve stem 166, which maybe incorporated into rotary valve 156 in FIG. 4A. Valve stem 166 is configured with a tapered sealing face and a pass-through conduit 135 of a predetermined volume. Valve stem 166 can be made of a soft, compliant material, such as Teflon or polypropylene, which allows for a seal without the need for a gasket or sealing grease. The valve could also be manufactured with an over molded sealing gasket made of silicone, Viton, or other compliant material. The valve could also be made of a non-compliant material that can be made with a ultra-smooth surface finish, such as ceramic or Delrin to make a seal. A retractable motorized keyed drive, such as a screwdriver blade in the analyzer, which fits into a slot 137, rotates the valve stem 166. In alternate embodiments valve stem 166 could be rotated in other ways, such as magnetically or pneumatically. While the movable valve that is shown is a rotating valve type, other configurations could also be used, such as a slide valve, an on-off valve, or a removable partition. Alternate embodiments of the valve may be employed, which separate the fluidic and metering functions of the valve, utilizing a fixed dimensional channel to determine a metered sample volume.

Referring to FIGS. 2 and 6, the removable reagent supply module 170 provides diluent-stain and/or a vacuum to the test cartridge 102. It is preferably a disposable item to be used in connection with several single-use test cartridges to ensure that the diluent-stain is fresh and uncontaminated. In one embodiment, the reagent supply module 170 includes a diluent metering or supply pump 126, a diluent channel 174, a vacuum pump 171, and a vacuum channel 172. In one embodiment, the reagent supply module 170 also includes a drip cup 176 for collecting any sample fluid that might leak through a cartridge's sample collection opening 150.

Figure 7:
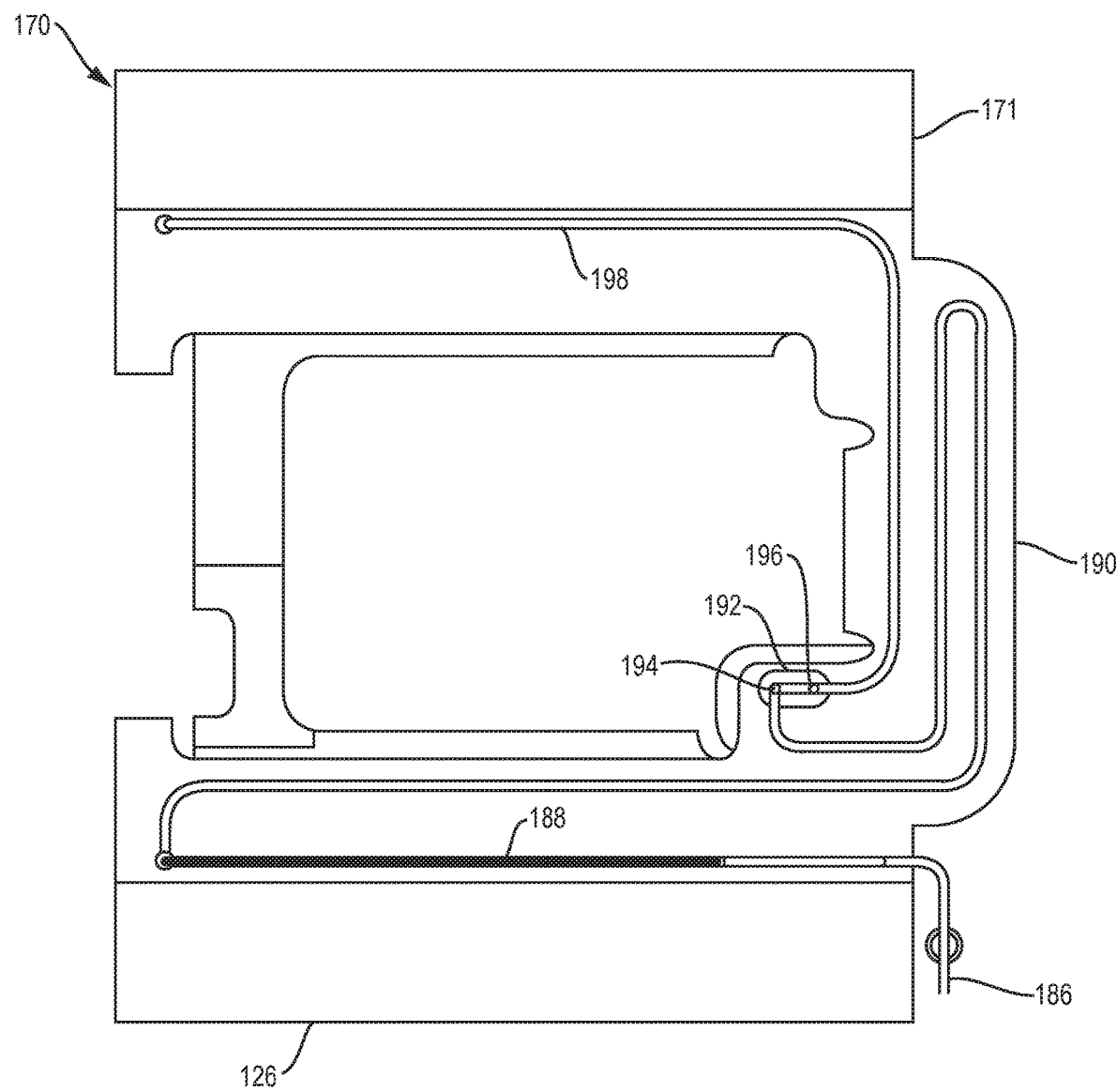
FIG. 7 is a plan view diagram of the illustrative reagent module of FIG. 6 shown without a cartridge in place and with initial priming.

Referring to FIG. 7, the reagent supply module 170 includes a series of channels that enable it to supply a precisely metered, bubble-free volume of diluent-stain to the cartridge. The diluent-stain volume is metered by first opening a vent valve 186 and advancing the piston in the cylinder of the diluent metering pump 126 to push a portion of diluent-stain in channel 188.

Figure 8:
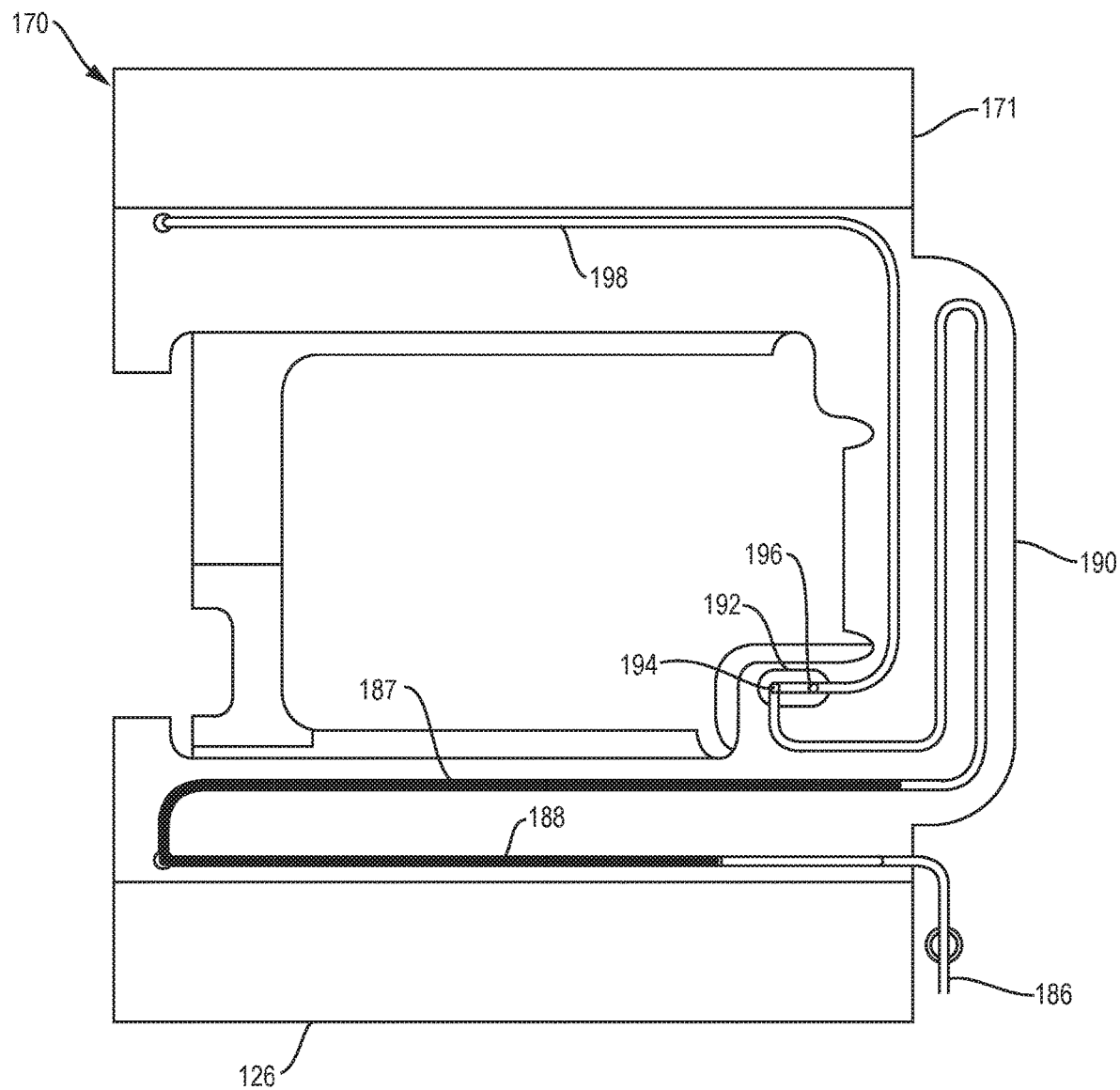
FIG. 8 is a plan view diagram of the reagent module of FIG. 7 shown with a first stage of diluent charge metering.

Referring to FIG. 8, the vacuum pump 171 is then actuated to draw a vacuum in channel 198 through the vacuum channel 172 (FIG. 6), while the diluent metering pump 126 remains on, causing diluent-stain to flow forward into a metering channel 187. The vent valve 186 is left open during this operation to prevent any pressure buildup.

Figure 9:
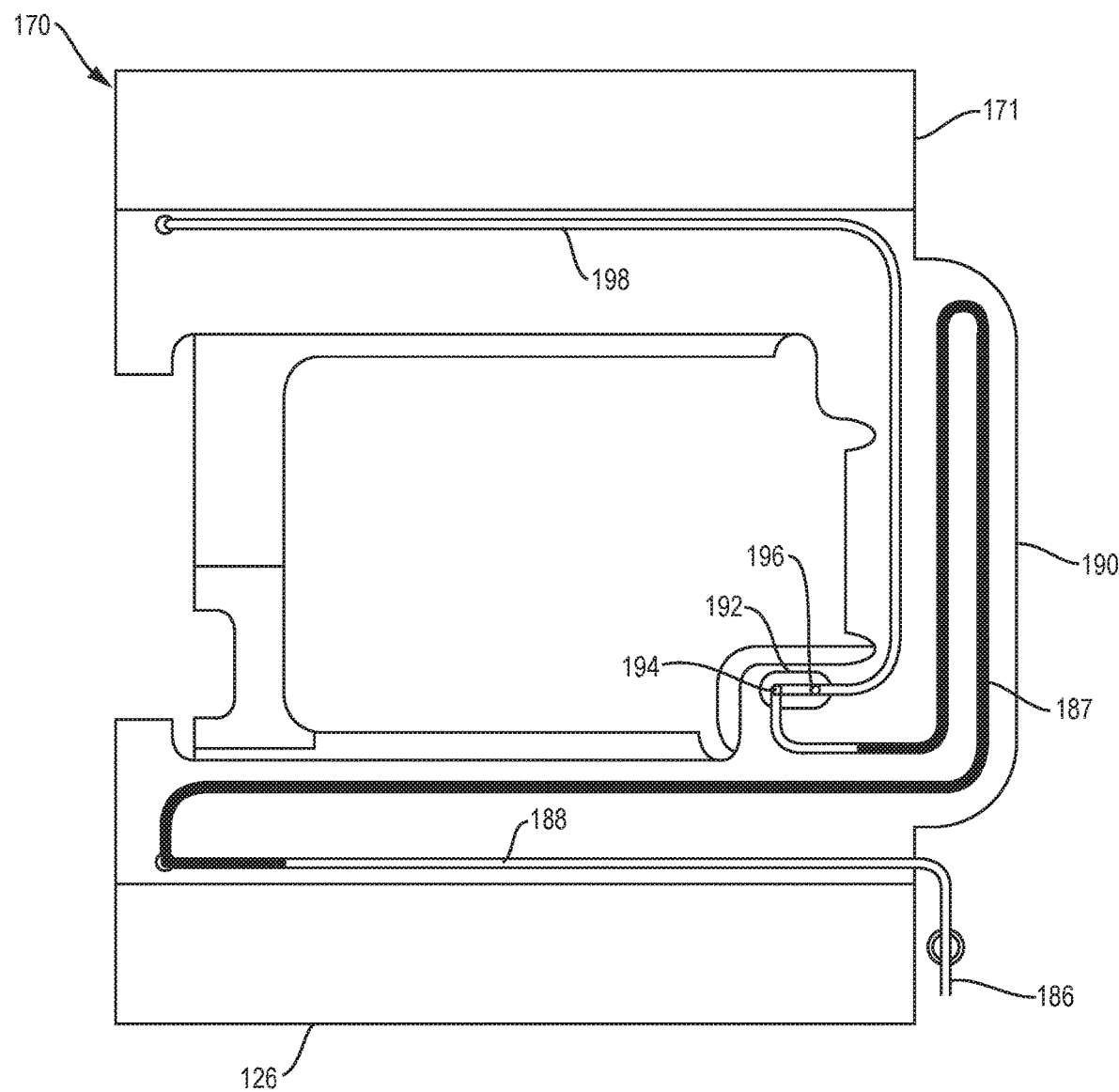
FIG. 9 is a plan view diagram of the reagent module of FIG. 7 showing a second stage of diluent charge metering.

Referring to FIG. 9, the diluent metering pump is then stopped with the vacuum pump 170 continuing to draw a vacuum, causing the diluent-stain to move forward in the metering channel 187.

Figure 10:
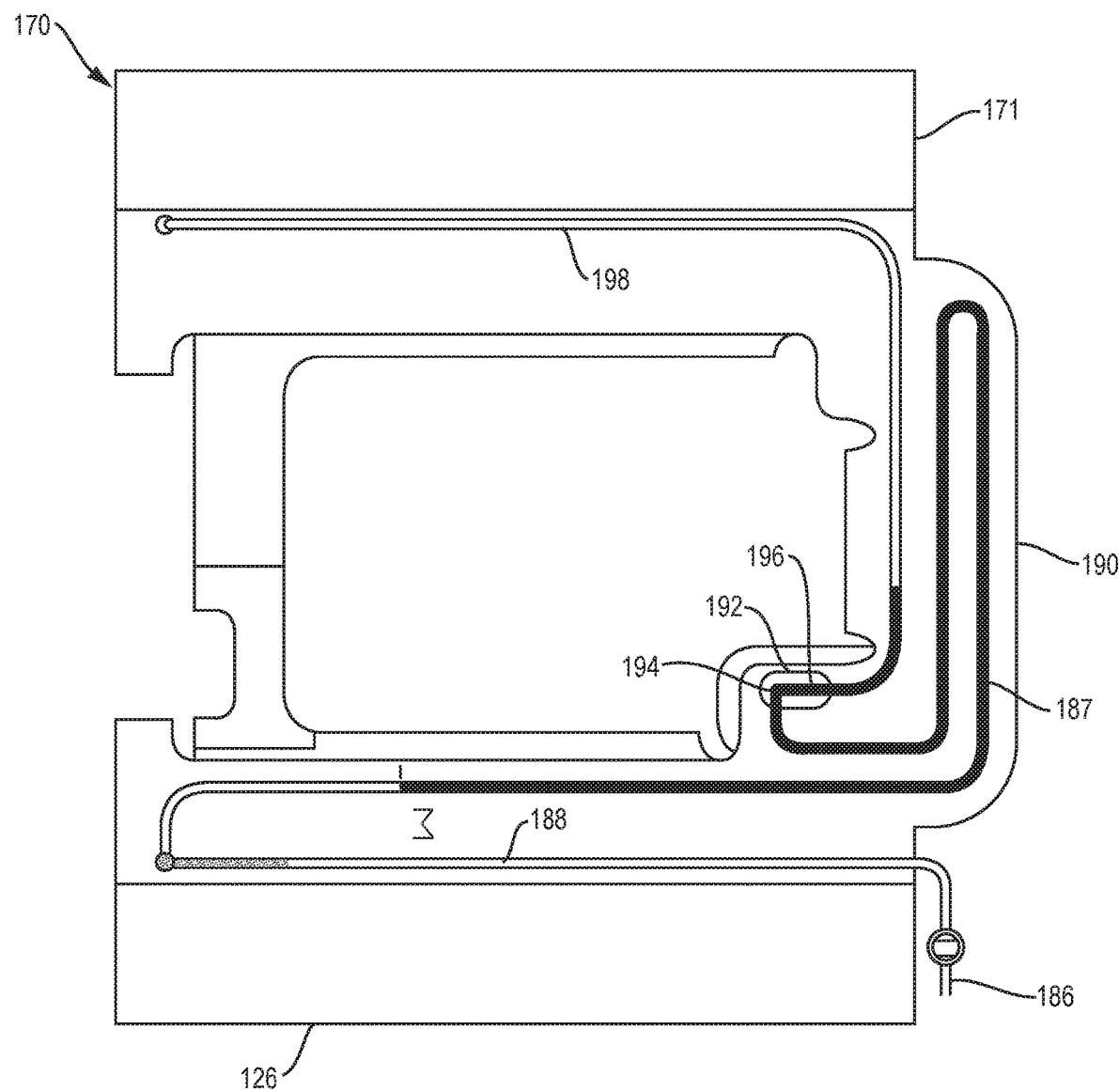
FIG. 10 is a plan view diagram of the reagent module of FIG. 7 after completed diluent charge metering.

Referring to FIG. 10, the vacuum pump pulls the diluent-stain charge past a diluent-stain output port 194 and then past a vacuum port 196. These ports correspond to, and interface respectively with, diluent-stain input port 160 and vacuum port 164 on the cartridge of FIG. 4A. This filling occurs, because a bypass valve 192 connects these two ports when the cartridge is not in place in the cradle. Allowing the diluent-stain to flow past the ports prevents bubbles from being formed at the reagent supply module/cartridge interface (i.e., the module is self-priming). It also allows the tail end of the diluent-stain to be precisely lined up with a mark "M" by a digital camera as described below to precisely determine the amount of fluid in the channel 187 between the mark and the diluent-stain intake port 160 on the cartridge. The bypass valve 192 can be a spring-loaded valve.

Once the metered diluent-stain charge is in place, the vent valve 186 is closed and the reagent supply module is in a primed state ready for a test. This charge can be drawn into the vacuum cylinder and the priming sequence can be repeated if bubbles form in the charge or it is left in the reagent supply module for too long and is deemed to be "stale."

Figure 11:
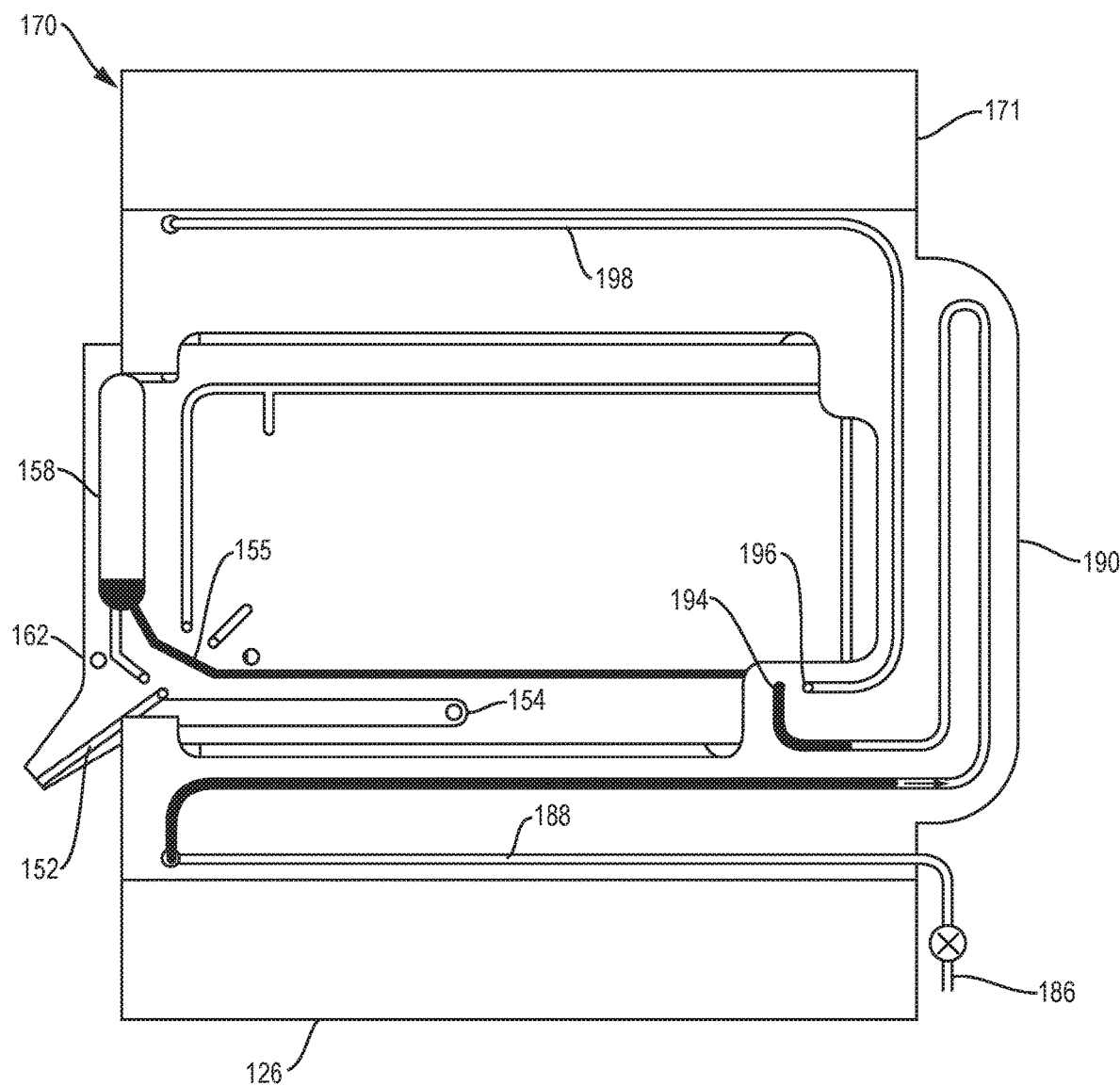
FIG. 11 is a plan view diagram of the reagent module of FIG. 7 shown with a test cartridge in place for diluent charge delivery.
Figure 12:
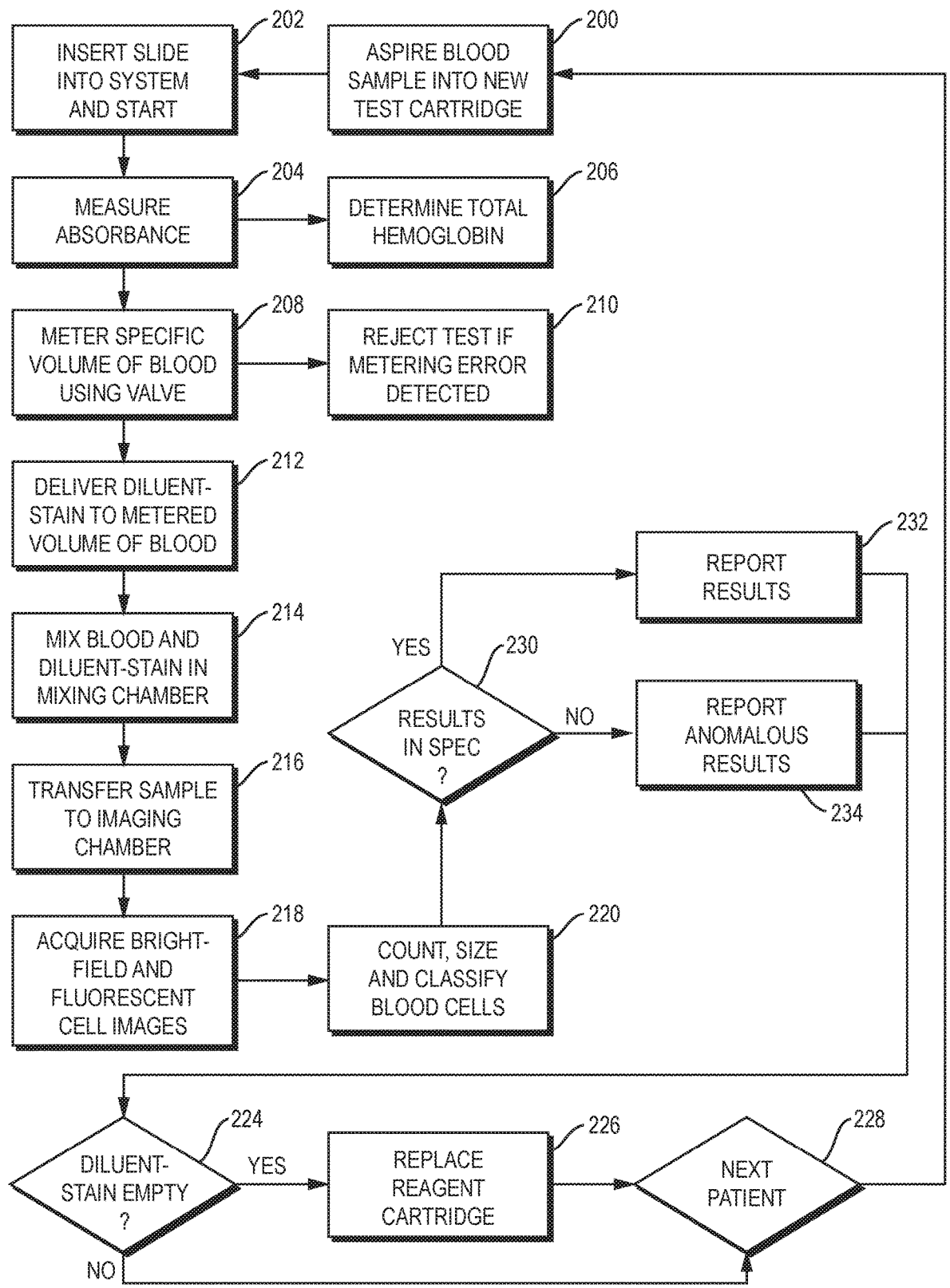
FIG. 12 is a flowchart illustrating the operation of the analyzer.

Referring to FIGS. 2, 6, and 11, when the test cartridge 102 is in the cradle 173 of the primed reagent supply module 170, and the valve is in the second flow position, the analyzer can engage the diluent metering pump to move the metered diluent-stain charge into the test cartridge, thereby pushing the sample in the pass-through conduit in the valve into the mixing chamber of the cartridge together with the diluent stain, as described in connection with FIGS. 3B and 4C. As the diluent-stain charge is used in this operation, the reagent supply and vacuum pumps can be operated to meter a second charge 228 (FIG. 12) behind the initial charge, so that the analyzer is left in a primed state and another test can be carried out immediately on the next test cartridge. It is noted the diluent-stain beyond vacuum port 196, and any incidentally aspirated fluids, will be safely held in the vacuum pump chamber until disposal of the reagent supply module.

In one embodiment, the reagent supply module 170 meters 80 uL of diluent-stain to be mixed with 2 uL of blood to achieve a 40:1 dilution ratio. Ratios between about 10:1 and 250:1 should allow most or all of the cells and platelets in any sample to be spaced out in the imaging chamber such that they do not clump or bunch or lie on top of themselves when they settle to the bottom of the imaging chamber and such that they can be imaged and counted by the digital camera.

The depth of the imaging chamber determines the minimum dilution ratio. The imaging chamber depth is optimized so that its depth is sufficiently large to accommodate various cell sizes and small enough that cells settle quickly. The dilution ratio is optimized so that cells do not clump or bunch or overlap at the highest cell concentration in the physiological range, so that the cells and platelets can be imaged and counted by the digital camera. In one embodiment, an imaging chamber depth of 100 um is used in combination with a 40:1 dilution ratio. If a smaller imaging chamber depth of 75 um is used, a 30:1 dilution ratio is acceptable to prevent cell crowding.

The minimum volume of diluted sample needed for analysis is determined by the dilution ratio and the desired number of total cells or platelets to be counted. For example, if 1000 white cells are needed for the low-end of the normal range (3000/uL) of whole blood and a dilution ratio of 30:1 is used, then 10 uL of diluted sample is needed for analysis. If a 40:1 dilution ratio is used, then 13.3 uL of diluted sample is necessary. The minimum volume of the diluted sample should also ensure a representative sample of the homogenous sample/diluent-stain mixture. To ensure accuracy of results for a CBC, the mixture should include a minimum of 0.25 uL of a whole blood sample.

The digital camera 124 (FIG. 2), in conjunction with software, is used to monitor the operations of the cartridge and reagent supply module in addition to acquiring images of the diluted sample in the imaging chamber. A separate digital camera could also provide this functionality. The camera may monitor the flow of fluids and detect bubbles, for example, or failures to provide sufficient diluent-stain. It may even act as the primary mechanism for measuring the diluent-stain, such as by detecting the length of fluid channels of known diameters or cross section dimensions that are filled with diluent-stain, and for the measuring the area spanned by the diluted sample in the imaging chamber.

A machine-readable depth indicator 125 (FIG. 2) may be incorporated in the analyzer to measure the depth of the imaging chamber and the photometric chamber, or a rectangular diluent-stain channel of the test cartridge, if they are utilized to meter the diluent. This may be accomplished by sending a differential laser signal through the objective lens or by incorporating a laser displacement measuring device in the analyzer. This indicator can determine a precise depth measurement at each point of the imaging chamber, where cell images are taken. A sampling of points may also be used to create a three-dimensional profile of the imaging region. Knowledge of the exact depth of the imaging region taken together with the area measurements of the sample/diluent stain mixture in the imaging chamber allows for a quantitative calculation of the volume of the sample/diluent-stain mixture that is imaged. One or more dimensions of the photometric chamber and the imaging chamber of the test cartridges can also be premeasured, such as after manufacture, and these measurements can be provided with the cartridges, such as in machine-readable barcodes 280 (see FIG. 14). These dimensions may also be fixed in the manufacturing process, but it is difficult to hold a fixed depth within these chambers with uniformity across all test cartridges. In a preferred embodiment of the present invention, all of the sample/diluent-stain mixture is transferred into the imaging chamber and all the cells and platelets are counted. In this case, only the volume of sample metered by the pass-through conduit need be known. There is no need to know the depth of the imaging chamber, the dilution ratio, or the area of the imaging chamber spanned by the sample/diluent-stain mixture. As such, the variations in physical dimensions from one test cartridge to another, except for the pass-through conduit, are not relevant, and the risk of error in results of the CBC test is minimized.

Figure 13:
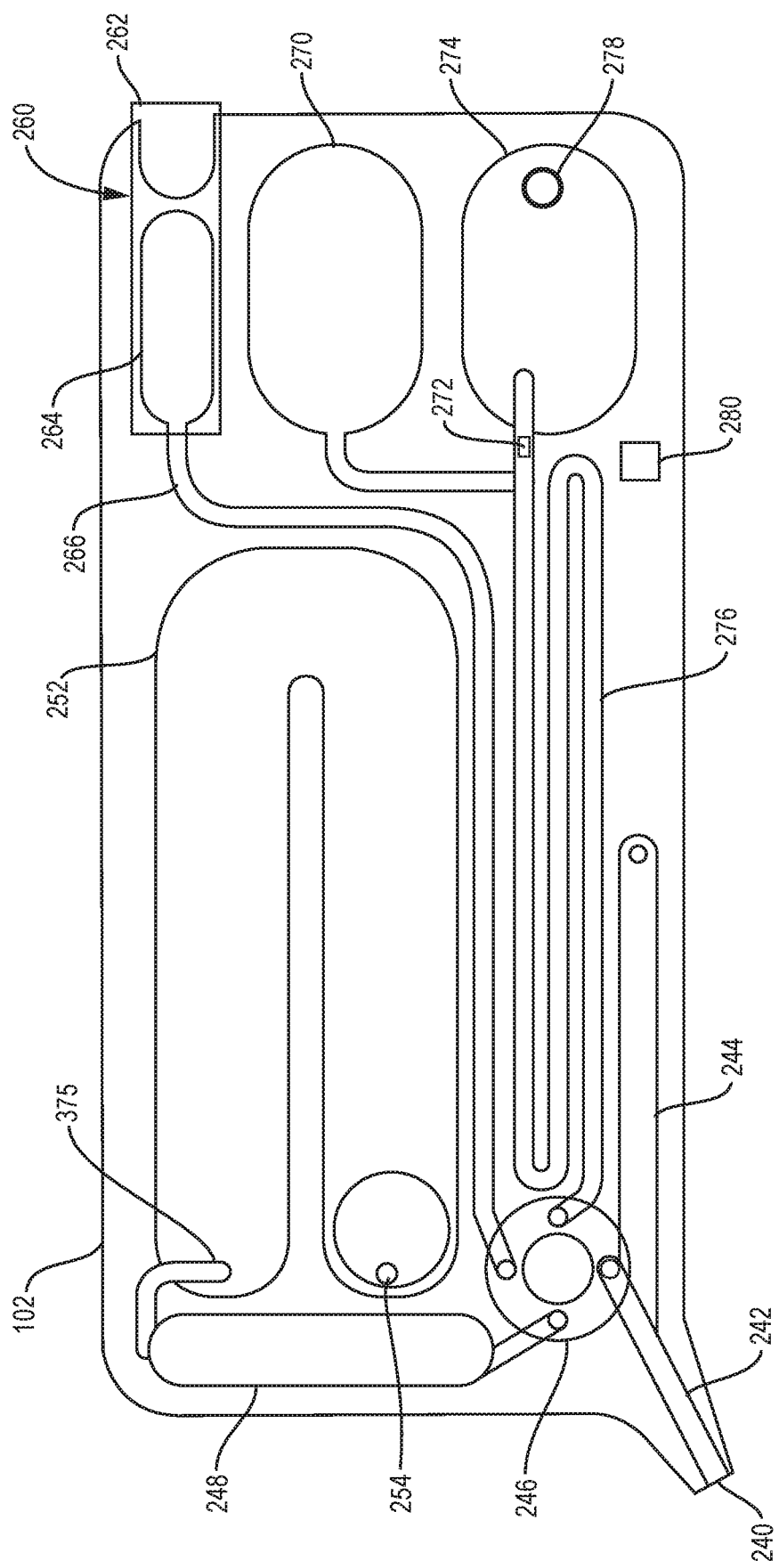
FIG. 13 is a plan view of a test cartridge with on-board reagents.
Figure 14:
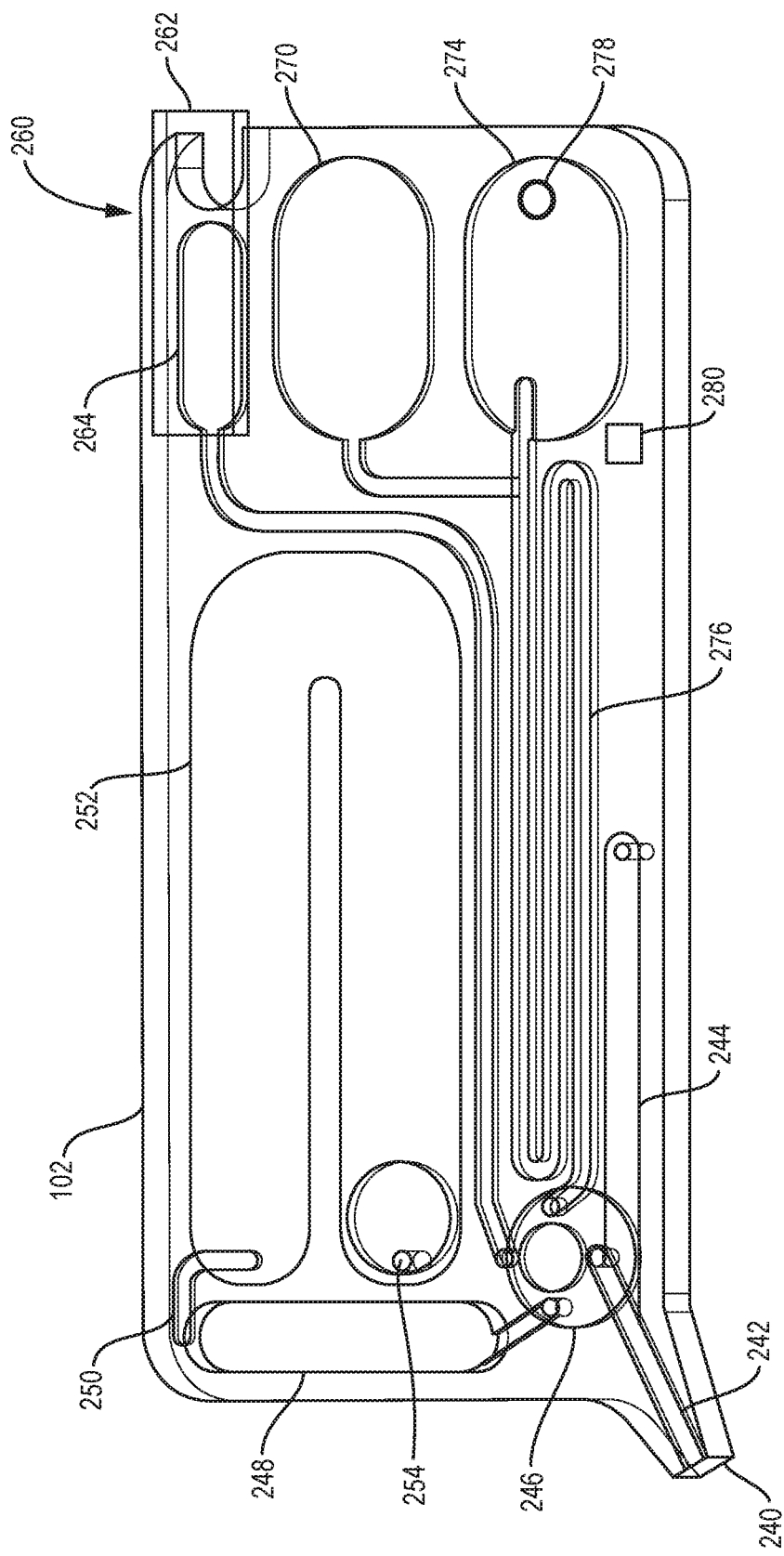
FIG. 14 is a perspective view of the cartridge of FIG. 13.

In an alternative embodiment, the diluent and stains may be incorporated in the test cartridge. They can be dispensed into a chamber in the test cartridge and sealed using a film or foil. They can also be supplied by a reagent blister pack that is added to the test cartridge. Referring to FIGS. 13 and 14, in one embodiment, a cartridge 102 employs a reagent chamber 274 for preloaded diluent-stain. The diluent-stain is added to the chamber, which is then sealed with a plastic film or aluminum foil covering, during manufacture.

Like the cartridge 102 shown in FIG. 4A, the test cartridge in FIG. 13, employs capillary action to draw a biological sample that includes cells, such as blood or other body fluids, into a sample collection port 240 and input channel 242 and photometric chamber 244.

The analyzer rotates the valve to a first flow position and the sample is drawn through the pass-through conduit into the valve 246 and into the vacuum channel 266 by suction from a vacuum pump 260. This vacuum pump includes a lever that is connected to a diaphragm over a vacuum chamber 264, and is activated by an actuation mechanism on the analyzer, such as a solenoid, cam, or linkage member. Other types of vacuum sources, such as a syringe-based pump, could also be substituted for this source, or a vacuum source from the analyzer could be used.

The analyzer then rotates the valve to a second flow position wherein the mixing chamber 248 is fluidically coupled to the pass-through conduit and the diluent-stain channel 276. This rotation traps a fixed amount of blood in the pass-through conduit of the valve, effectively causing it to act as a metering chamber. The metered blood sample can then be pushed by, and together with, a flow of diluent-stain from the diluent-stain chamber 274 into a mixing chamber 248. The diluent-stain and metered blood sample are mixed in the mixing chamber. The mixture, or a portion thereof, is moved into imaging chamber 252, which is connected to the mixing chamber by channel 375. The imaging chamber has vent 254 to allow air to escape when the sample/diluent-stain mixture, or portion thereof, is transferred from the mixing chamber to the imaging chamber as more fully explained below. The microscope obtains images of the blood cells and platelets in the imaging chamber. A photometric measurement, such as a hemoglobin measurement, can be performed on the sample in the photometric chamber 244.

In one embodiment, the diluent-stain is metered in an on-board channel 276 in a manner similar to the metering of diluent-stain that is discussed above in connection with the test cartridge and reagent supply module illustrated in FIGS. 6-11. More specifically, diluent-stain is pushed e.g., by pressure applied through an opening 278 in the reagent supply chamber 274, along the diluent channel 276. The analyzer can expel a plug 272 that keeps the diluent-stain in the reagent supply chamber when it is stored. When the diluent-stain mixture has progressed to the valve 246, as detected by the digital camera, the flow is stopped, and an air pump 270 introduces an air bubble in the line to isolate a metered amount of diluent-stain. When the digital camera detects the air bubble, the pushing is stopped, and the diluent-stain and blood are mixed in the mixing chamber. After the mixing is completed, the mixture or a portion thereof, is pushed or pulled into the imaging chamber 252. Where all of the mixture is transferred into the imaging chamber and all the cells and platelets are counted, it is not necessary to meter the amount of diluent-stain or to know the dilution ratio.

Figure 15:
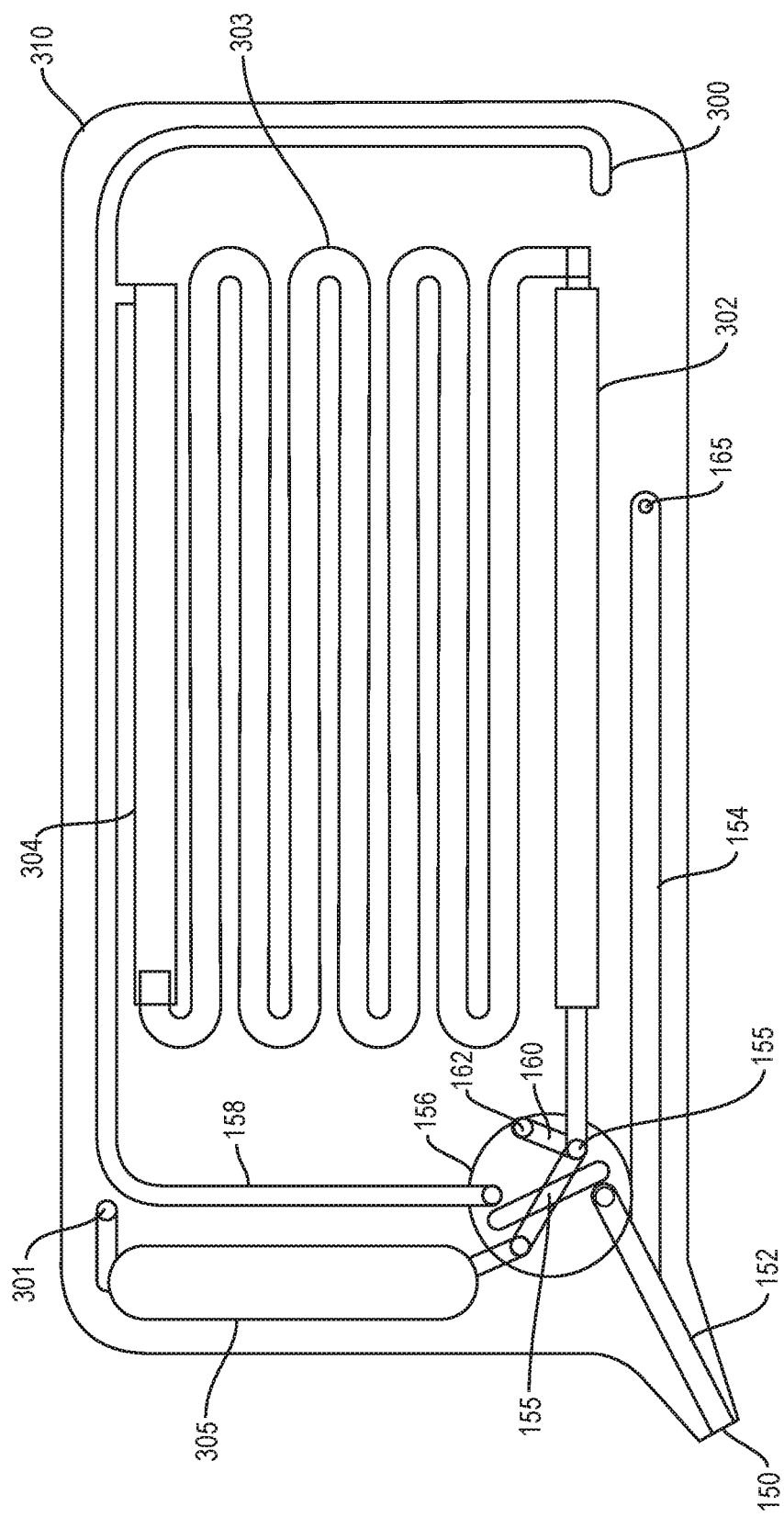
FIG. 15 is a perspective view of a test cartridge with on-board reagents and a passive mixer.

A third type of test cartridge 310 is illustrated in FIG. 15. In this case, passive mixing chambers or channels 302 and 304 are connected to the imaging chamber 303 and the sample is mixed in the passive mixing chambers as well as in the imaging chamber. In test cartridge 310, the entire metered volume of sample is transferred to the imaging chamber and every cell and platelet is counted. In this embodiment, the sample enters the collection port 150 and is drawn by capillary action into the input channel 152 and the photometric chamber 154. The photometric chamber includes a vent 165, such as a hydrophobic vent, at the distal end to enable the input channel 152 and photometric chamber 15 to fill themselves from the input channel 152 by capillary action. The rotary valve 156 contains a pass-through conduit 155 of a predetermined volume. In determining the volume of the pass-through conduit, one should take into consideration the time it takes the automated microscope to count cells, as every cell in the sample trapped by the pass-through conduit is counted in this embodiment. One should also consider a minimum volume of sample to insure a representative sample such that it will correlate to an intravenous sample as measured on a predicate method such as impedancemtry or flow cytometry. At the same time, one must also take into consideration the repeatability of the volume of the pass-through conduit of the rotary valve from test cartridge to test cartridge. It may be difficult to accurately and repeatedly manufacture a volume of less than 2 uL. To initiate testing of a sample, the rotary valve is turned to a first flow position wherein the pass-through conduit is fluidically coupled to the input channel 152 and a vacuum channel 158. The sample is drawn through the pass-through conduit 155 in rotary valve 156 by a vacuum source connected to port 300. The vacuum source may be contained in the analyzer, such as in the reagent supply module 170 (FIG. 6). The sample fills the pass-through conduit 155 so that when the valve turns, a predetermined volume of blood is isolated. The diluent-stain is then supplied to diluent chamber 305 by reagent supply module 170 (FIG. 6) through port 301. The diluent-stain could also be packaged on board the test cartridge either by use of a reagent blister or by adding it to a chamber in the cartridge. Alternatively, the diluent-stain could be added to a reservoir in the test cartridge by the operator prior to the commencement of the dilution step. The valve is turned to a second flow position where the pass-through conduit 155 is fluidically coupled with the diluent chamber 305 and fluidically coupled with a first passive mixing chamber 302. The diluent-stain is pushed by a diluent metering pump or pressure source in the reagent supply module connected to the diluent chamber 305 at port 301, so that the diluent-stain passes through the pass-through conduit 155 in rotary valve 156 to flush the entire sample into the first passive mixing chamber 302. When all of the sample has been completely washed out of the pass-through conduit, the valve rotates to a third flow position where a connecting conduit 160 in the valve 156 fluidically connects the first passive mixing chamber 302 with a hydrophobic vent 162, which is open to the atmosphere. Empirical studies have determined that a volume of the diluent-stain that is in excess of 3-times the volume of the pass-through conduit 155 is sufficient to wash out all the isolated sample of the rotary valve 156. Therefore, the volume of diluent-stain dispensed from the reagent supply module should be chosen to provide any desired dilution ratio greater than 3:1. With the valve in the third flow position, a vacuum is applied to port 300 to pull the sample and diluent-stain from the first passive mixing chamber through the imaging region 303 and into a second passive mixing chamber 304. The sample is then pushed back to the first passive mixing chamber 302 by a pressure supplied to port 300. This process of pushing and pulling is repeated until the sample is mixed and there is no clumping or overlapping of cells. The number of pushing and pulling cycles will depend upon the hematocrit of the sample, the geometric shape and the width and depth of the imaging chamber, and the velocity of the mixture in the pulling and pushing action and other factors. A macroscopic camera may be used to check the mixture. Empirical studies may also determine the number of pushing and pulling cycles for any particular imaging chamber over the range of sample hematocrit in the physiological range. It is possible that only one mixing cycle of pushing and pulling is needed to mix the sample and diluent-reagent and present the cells for imaging without clumping or overlapping. Thereafter, the sample/diluent-stain mixture is positioned such that it is entirely within the imaging region 303, and not in either passive mixing chamber. The imaging chamber includes channels that preferably have a width of 0.5 mm to 3 mm. In choosing the dilution ratio of diluent-stain to sample, the amount of diluent-stain must be sufficient to dilute the sample such that there is no clumping or overlapping of cells when the cells settle to the bottom of the imaging chamber. The total volume of the imaging chamber must also be taken into consideration, as the mixture of sample and diluent-stain must not exceed the volume of the imaging chamber. All of these considerations, as well as the physiological range of the number of cells, platelets, and hemoglobin of the sample to be tested, must be taken into consideration in the design of the test cartridge. The exact amount of diluent-stain that is metered and dispensed by the reagent supply module is not critical in this embodiment of the invention, as all the cells and platelets in the sample are counted and the volume of the sample is known. The digital camera 124 (FIG. 2) monitors the movement of the sample/diluent-stain in the passive mixing chambers and the imaging chamber. The mixture needs not to be homogeneous, since every cell and platelet is counted in the entire mixture. Since the volume of the sample is known, as is determined by the volume of the pass-through conduit in the valve, the number of cells and platelets per unit volume of sample can be determined. An alternate embodiment of the test cartridge presented in FIG. 15 uses a diluent-stain stored in the test cartridge. In this embodiment, the diluent-stain is stored in the diluent chamber 305. An external source can supply pressure to the diluent storage chamber 305 to push the diluent-stain through the pass-through conduit of the rotary valve. Alternatively, a vacuum source connected to port 300 could be used to pull the sample into the pass-through conduit 155 and diluent-stain from a vented diluent storage chamber and into the first passive mixing chamber 302. Where the diluent-stain is stored on the cartridge, there is no need for a removable reagent supply module containing the diluent-stain mixture. In this case, the analyzer may contain a fixed cradle to receive the test cartridge and contain vacuum and pressure sources that interface with port 300 on the test cartridge.

Figure 16:
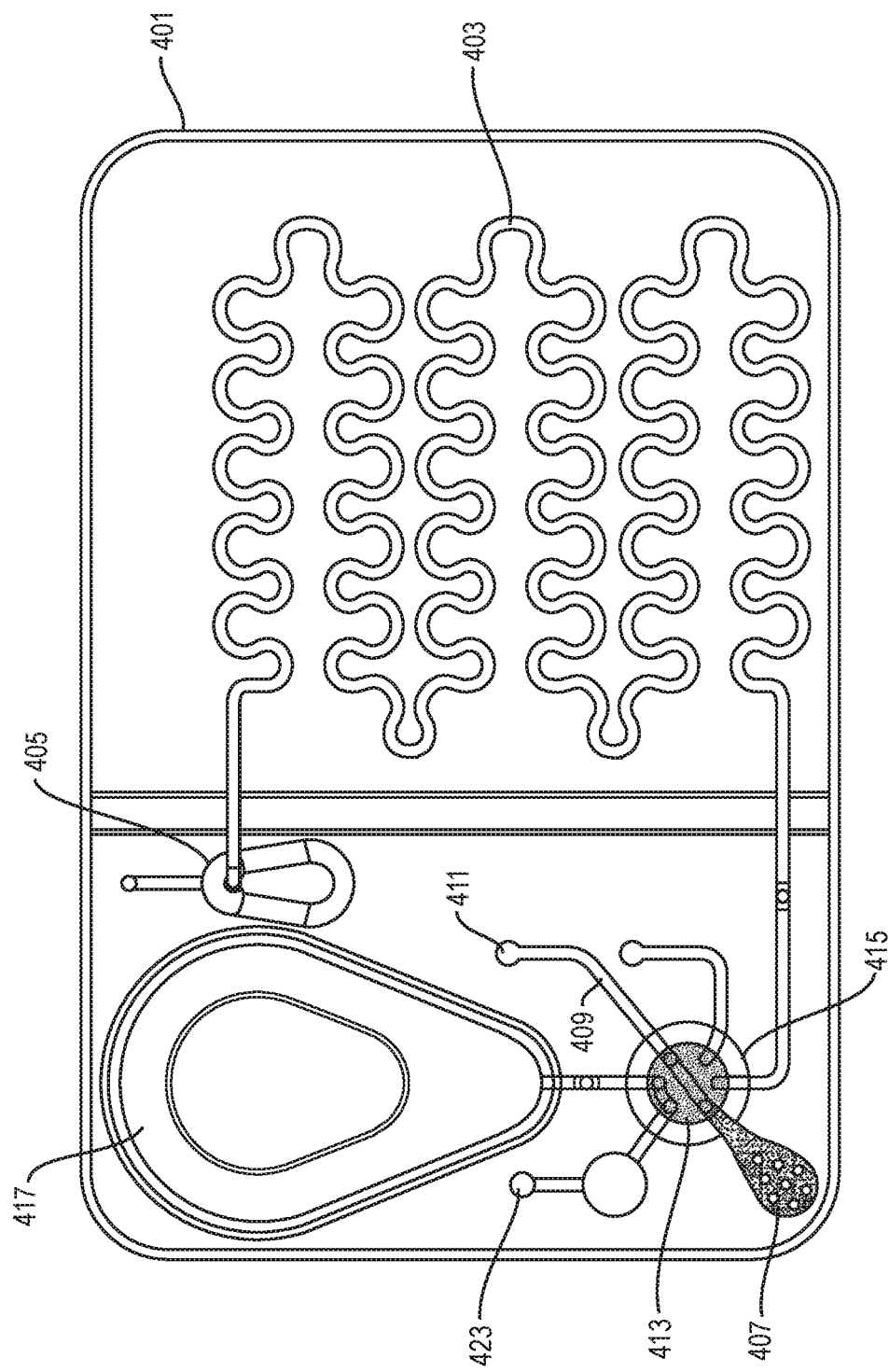
FIG. 16 is a plan view of a test cartridge with a serpentine imaging chamber and passive mixing chamber.

Another embodiment of a third type cartridge is illustrated in FIGS. 16-22. The test cartridge 401 includes a serpentine or wavy imaging chamber 403 and a passive mixing chamber 405. A sample is deposited in a sample collection port 407 (FIG. 16). A vacuum, supplied by the analyzer to a sample aspiration port 411, draws the sample into the pass-through conduit 413 and photometric chamber 409, when the rotary valve 415 is in a first flow position.

Figure 17:
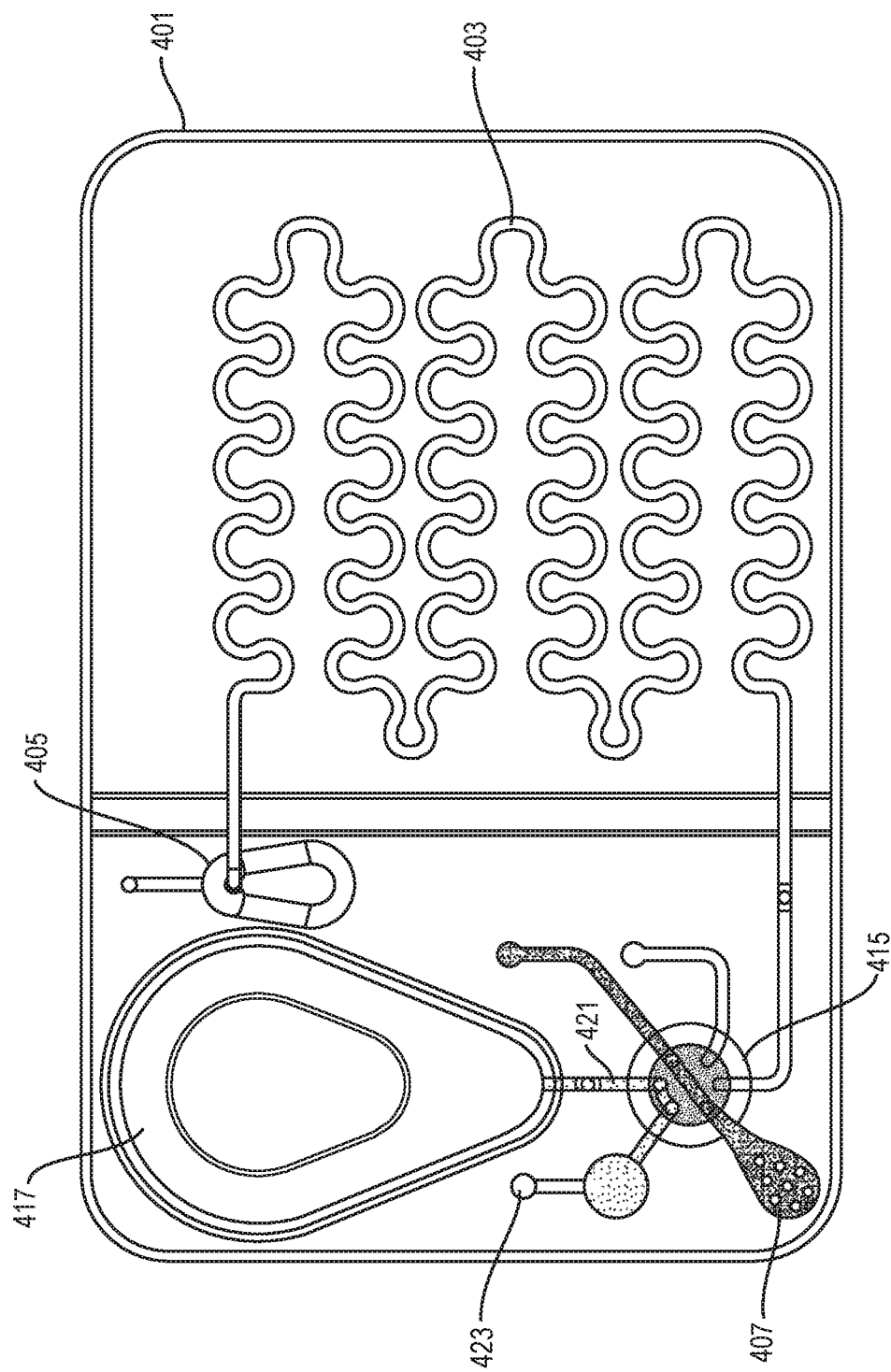
FIG. 17 is plan view of the cartridge of FIG. 16 with valve in the first flow position.
Figure 18:
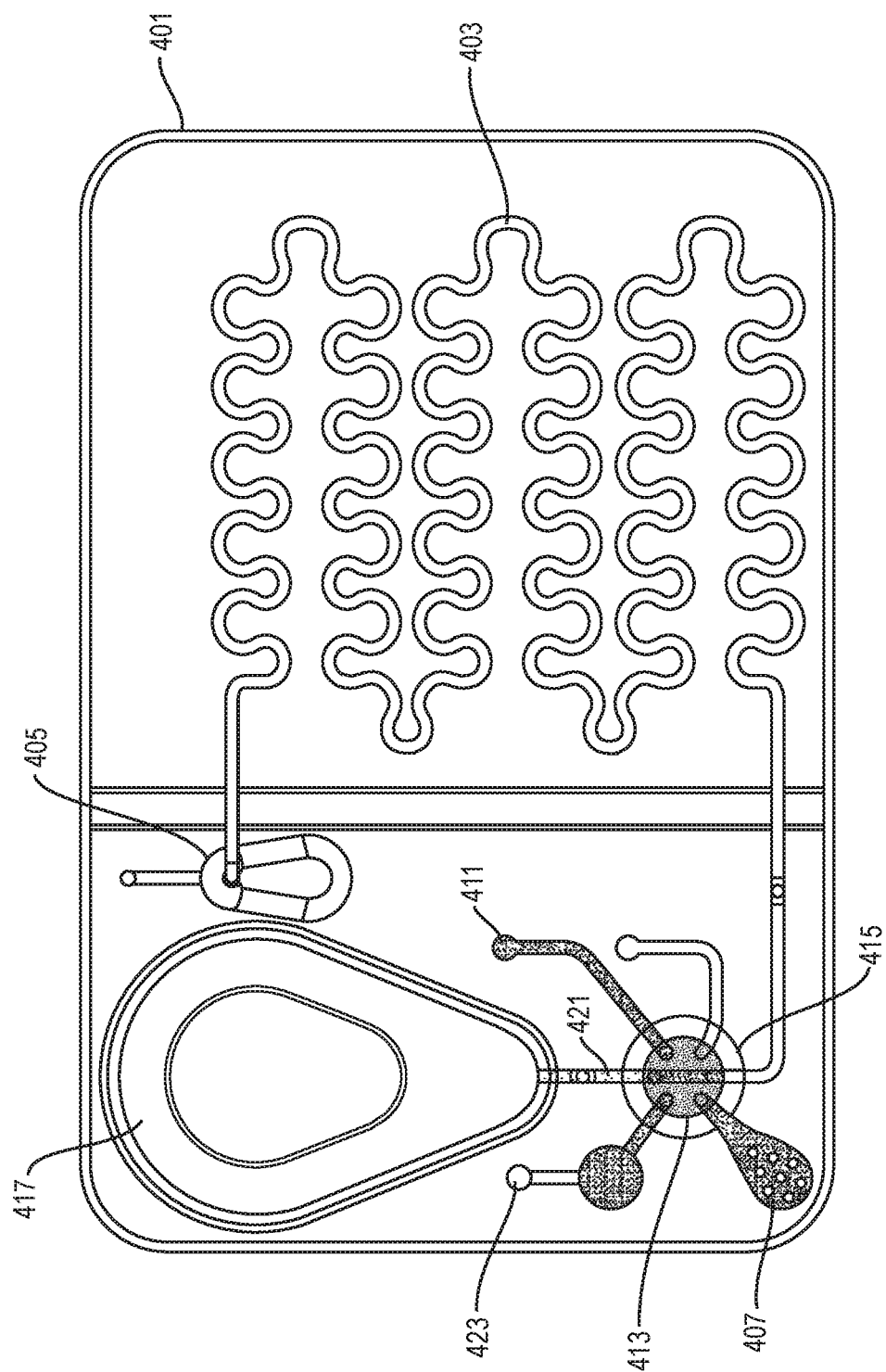
FIG. 18 is a plan view of the test cartridge of FIG. 16 with the valve in the second flow position.

The cartridge 401 contains an on board diluent-stain in a blister pack 417. The blister pack is fluidically coupled to a first vent 423 when the valve is in the first flow position. When pressure is applied to the blister pack 417 by the analyzer, diluent-stain is released and flushed through a connecting channel 421 (FIG. 17) and connecting channel 422 in the valve. Any air is bled from the connecting channels 421,422 through the first vent 423 (FIG. 17).

Figure 19:
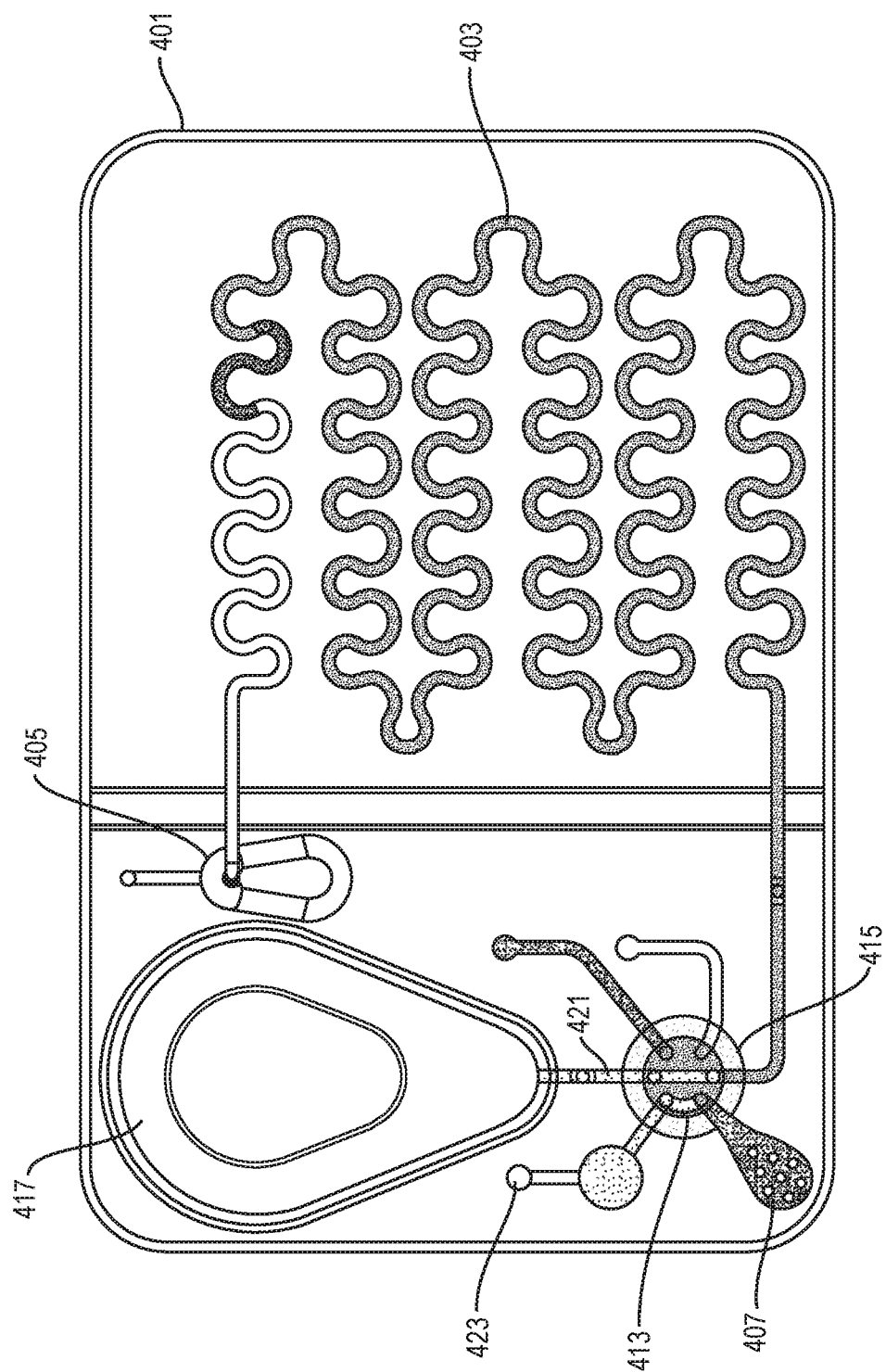
FIG. 19 is a plan view of the test cartridge of FIG. 16 illustrating the sample and diluent-stain in the imaging chamber.

When the rotary valve is turned to a second flow position (FIG. 18), it traps a predetermined amount of sample in the pass-through conduit 413. When it is in the second flow position, the blister pack 417 is fluidically coupled to the pass-through conduit 413 and the imaging chamber 403. When the analyzer supplies pressure to the blister pack 417, diluent-stain pushes the blood sample in the flow-through conduit 413 into the imaging chamber 403 (FIG. 19). The diluent-stain is pushed until the desired dilution ratio of diluent-stain to sample is obtained. As explained above, the ratio of diluent-stain to sample must exceed 3:1 to flush the entire sample completely out of the pass-through conduit 413.

Figure 20:
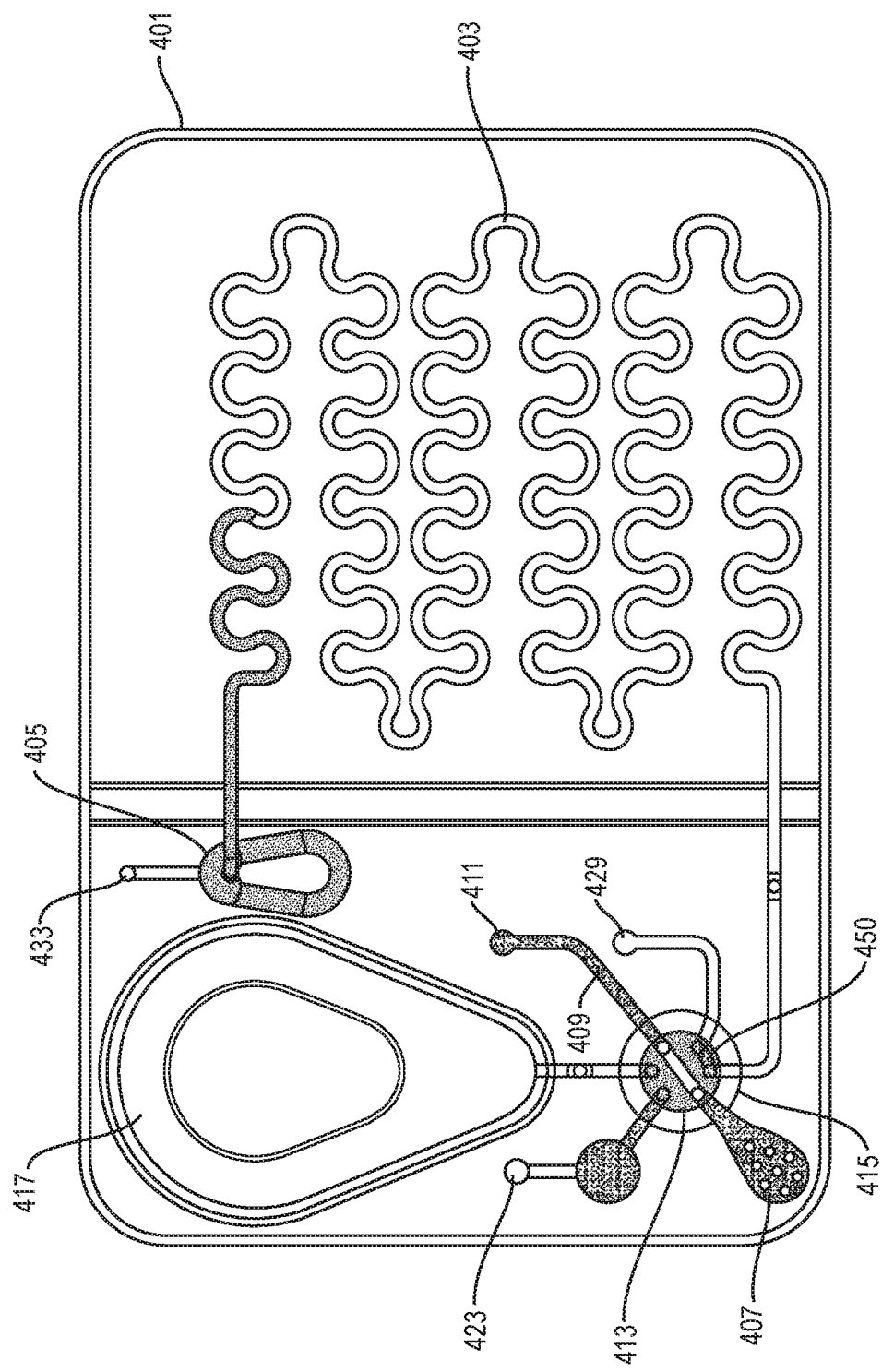
FIG. 20 is a plan view of the test cartridge of FIG. 16 illustrating the sample and diluent-stain partially in the passive mixing chamber.

The valve 415 is then turned back to the first flow position as illustrated in FIG. 20, and a bidirectional driving port 429 is fluidically coupled to the imaging chamber 403 through a channel 450 in the rotary valve 415. The analyzer supplies pressure to the driving port 429 and pushes all of the sample/diluent-stain from the imaging chamber 403 into the passive mixing chamber 405, which is vented by a second vent 433 (FIG. 20). Vacuum is then supplied at the bidirectional port 429, and the sample/diluent-stain mixture is pulled back into the imaging chamber 403. This process of pushing the sample/diluent mixture into the passive mixing chamber 405 and pulling the sample/diluent mixture back into the imaging chamber 403 is repeated until the mixture is free from cell clumping and overlapping.

The shape of imaging chamber 403 is wavy or serpentine, to minimize clumping and overlapping of the cells and to permit some mixing of the sample and diluent-stain in the imaging chamber. In one embodiment, the width of the serpentine channel may be between 0.5 mm and 2.5 mm and the depth may be from 10 to 200 um, and the dilution ratio may be from 10:1 to 100:1. When all of the sample/diluent-stain mixture is positioned in the imaging chamber 403 (FIG. 21), the valve is then rotated to a first closed position whereby the pass-through conduit 413 and vent 429 are no longer fluidically coupled to the imaging chamber 403, and images are taken of the entire imaging chamber 403 for analysis.

In choosing the dilution ratio of diluent-stain to sample, the amount of diluent-stain must be sufficient to dilute the sample such that there is no clumping or overlapping of cells when the cells settle to the bottom of the imaging chamber at the highest cell concentration in the physiological range.

The total volume of the imaging chamber 403 must also be taken into consideration, as the mixture of sample and diluent-stain must not exceed its volume. For example, if 1 uL is the volume of the pass through conduit and a dilution ratio of 40:1 is desired, the volume of the passive mixing chamber must exceed 41 uL. All of these considerations, as well as the volume of the pass-through conduit, must be taken into consideration in the design of the test cartridge 401. The exact amount of diluent-stain that is metered and dispensed from the blister pack 417 is not critical in this embodiment, as all the cells and platelets in the sample are counted and the volume of the sample is known. The digital camera 124 (FIG. 2) monitors the movement of the sample/diluent-stain mixture and positioning it in the imaging chamber 403. The mixture does not need to be homogeneous, since every cell and platelet is counted in the entire mixture. Since the volume of the sample is known, the number of cells and platelets per unit volume of sample can be determined.

Figure 21:
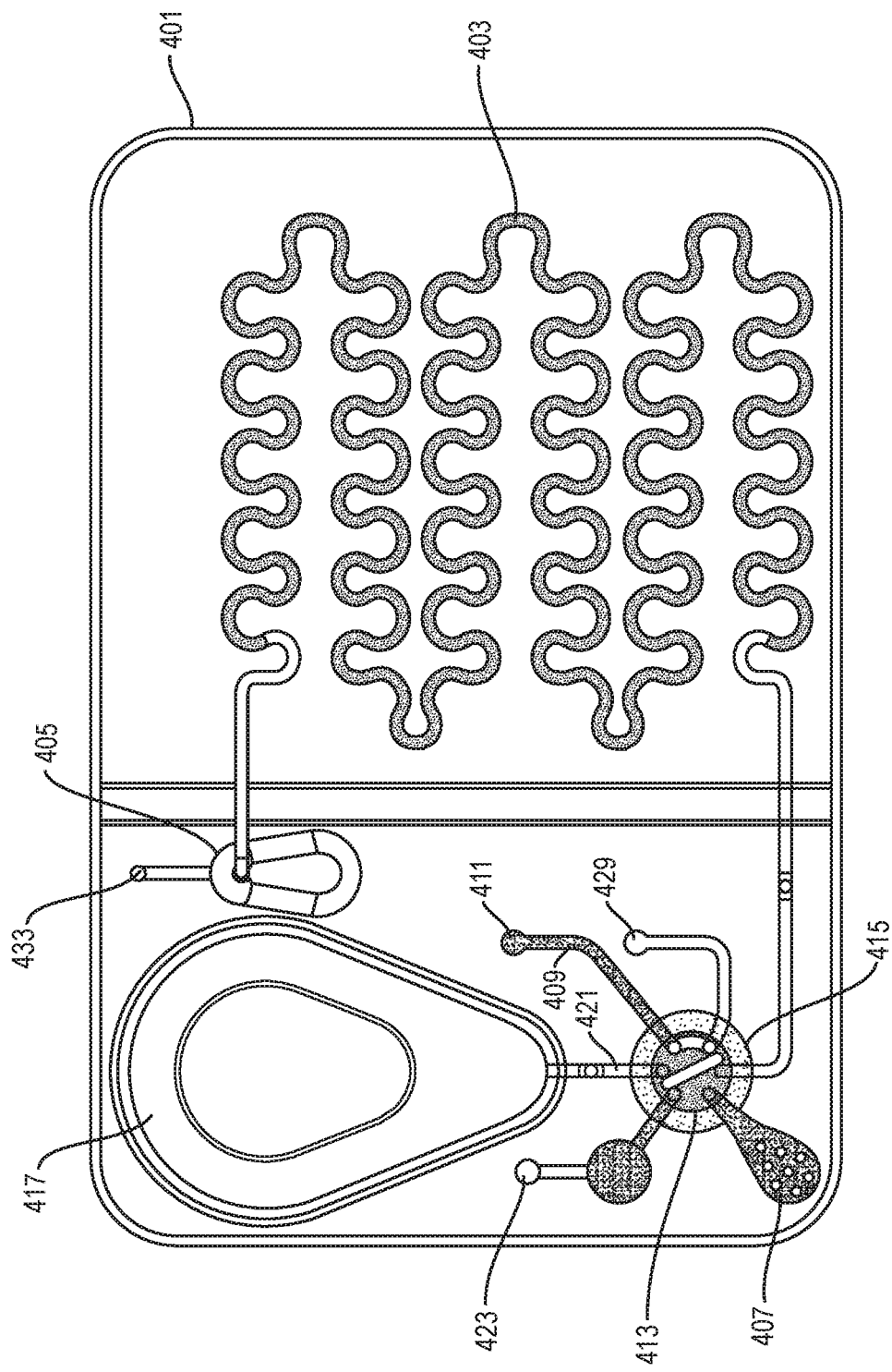
FIG. 21 is a plan view of the test cartridge of FIG. 16 with the sample/diluent-stain mixture positioned in the imaging chamber for analysis.
Figure 22:
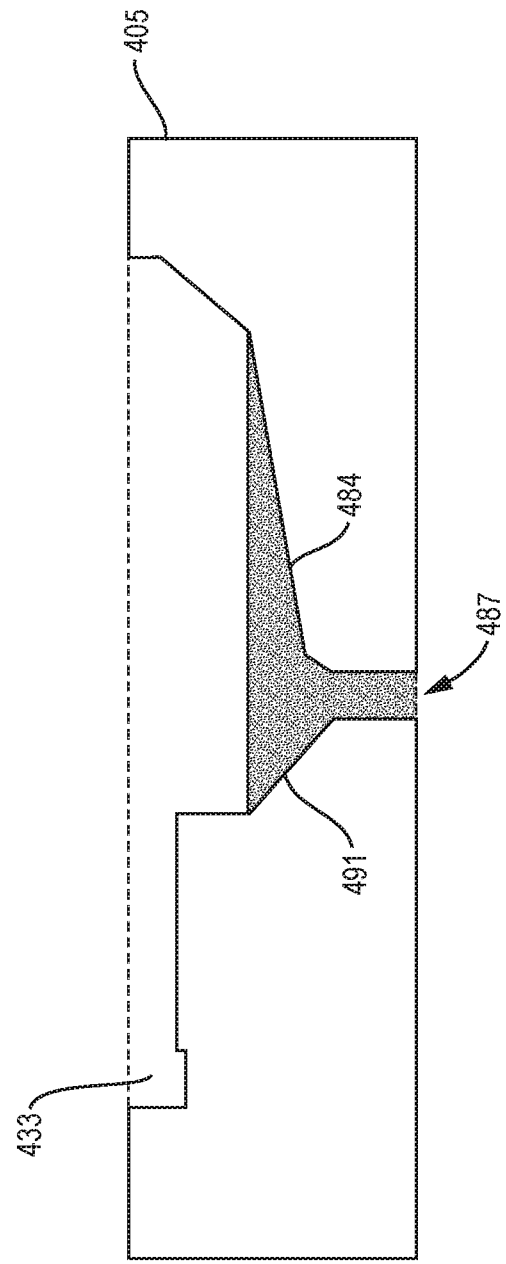
FIG. 22 is a plan view of a cross section of the passive mixing chamber in the test cartridge of FIG. 16.

The passive mixing chamber 405 depicted in FIGS. 21-22, has a horizontal cross section oval in shape and has a vertical axis perpendicular to the plane of the test cartridge 401. A vertical cross section of the passive mixing chamber 405 is illustrated in FIG. 22. The sample/diluent-stain mixture enters through opening 487 and air escapes through vent 433. The sample/diluent-stain mixture also empties out of passive mixing chamber 405 through opening 487. The cross section is asymmetrical to promote mixing of the sample and diluent-stain and for removing bubbles from the mixture. The bottom of the mixing chamber has sloped sides 489 and 491 so that all of the mixture empties out through opening 487, when it is pulled back into the imaging chamber 403 by the analyzer. The plastics utilized in the passive mixing chamber are conducive to all of the mixture empting out of the chamber when drawn back into the imaging chamber 403. The passive mixing chamber 405 illustrated in FIG. 22 is asymmetrical, but it need not be so. It may be of a different shape, providing it mixes the sample and diluent-stain and removes bubbles, and further providing that when the mixture is pulled back into the imaging chamber, all of the mixture empties out of the passive mixing chamber.

Preferably, the system 100 (FIG. 1A) is programmed to perform a Complete Blood Count (CBC). Generally, the CBC includes:
Red blood cell count (RBC),
White blood cell count (WBC),
Hemoglobin concentration in the blood,
Fraction of the blood composed of red blood cells (hematocrit),
A measure of average red blood cell size (MCV), a measure of the amount of
Hemoglobin per red blood cell (MCH),
A measure of the amount of hemoglobin relative to the size of the cell (hemoglobin concentration) per red blood cell (MCHC), and a
Platelet Count
The CBC is described in more detail in Hematology: Principles and Procedures, Chapter 2, by Barbara A. Brown, Lee & Fibiger, Fourth Edition (1984). The CBC may also include a measurement of reticulocytes (RETIC), nucleated RBC (nRBC), and immature cells (IC) per unit volume.

To obtain the CBC in one embodiment, the analyzer 100 uses a membrane-permeable dye, such as Acridine orange to differentially stain DNA and RNA of cells in whole blood. A plurality of stains can also be used to stain the blood cells. A combination of bright-field and fluorescent optics can be used to enumerate, size, and classify leukocytes, erythrocytes, and thrombocytes. In leukocytes, for example, Acridine orange exhibits green fluorescent emission for nuclear material and orange-red for cytoplasm. Using these two emission patterns, cell segmentation and classification can be performed by software in a computer that is preferably located inside the analyzer housing 106 (FIG. 1A). Platelets will also fluoresce with orange-red emission. The RBC will not fluoresce unless they are nucleated, such as with erythroblasts (nRBC) or if they are reticulated.

In this embodiment, the CBC is obtained from analysis of approximately 10,000 bright-field and fluorescent five-megapixel images (a total of 20,000 images) at a 20× magnification for a 3 uL sample volume and a forty to one dilution ratio. The analyzer may count more or less images if a larger or smaller camera sensor size, or magnification, is utilized. Similarly, the number of required images to count all the cells is affected by a larger or smaller dilution ratio. The minimum number of images collected is selected to count a desired minimum number of cells or platelets. In particular, the cells that are fewest in number, the WBC, determine the minimum number of images required to provide an accurate count. The accuracy of the WBC count and WBC Differential will be related to the number of images taken.

As noted above, the cell distribution throughout the imaging region may or may not be homogeneous, depending upon the geometry and dimensions of the imaging chamber, the time for dispensing the mixture from the mixing chamber into the imaging chamber, the physical forces between the cells and plastic walls of the imaging chamber, the amount of the mixture in the imaging chamber, the dilution ratio, and many other factors. Where the mixture in the imaging chamber is not homogeneous or the changes in cell density from frame to frame is not relatively small, all the cells and platelets must be counted to insure accuracy. Alternatively, where the changes in cell density from frame to frame are relatively small, a sampling of cells to model the distribution of cells in the imaging chamber may be performed. In this case, counting all the cells and platelets in every other frame and doubling the count may be equivalent of counting every cell and platelet. The changes in cell density from frame to frame are minimized by the use of a serpentine or wavy imaging chamber, and its use is preferred for this reason. Alternatively, the imaging chamber may be segmented, and counting all the cells and platelets in every other segment, or every third or fourth segment, and adjusting the count appropriately may be statistically equivalent to counting every cell and platelet. The number of segments will be minimized with the use of a serpentine or wavy imaging chamber, and its use is preferred for this reason. For example, typically it is sufficient to take only 2000 images, or 10% of the cells, to determine accurate counts instead of 20,000 images at a 20× magnification for a 3 uL sample and a forty to one dilution ration. If after the completion of the scan there is not enough of a particular cell or platelet population to determine an accurate count, then additional images can be taken. This method may be used to improve counting statistics in the instances of patient samples with low concentrations of cells or platelets.

If a statistically significant sampling is taken, it must not only be a representative sample of the cell concentration, but also must take into account partial frames that include area inside and outside the imaging chamber where the frames overlap the boundaries of the imaging chamber. In these instances, there are two preferred methods to compensate for the partial frames. In one method, the sampling is chosen to take an equal portion of partial frames that would represent the total imaging region. In another, a region of interest (ROI) could be calculated for each frame to scale the partial frame to a full frame. The ROI calculation would then be used in conjunction with a macroscopic view camera that calculates the total area of the imaging region occupied by the diluted sample. If a statistically significant sampling is utilized, the minimum number of images collected must also be sufficient to count a minimum desired number of cells, and in particular, the WBC.

The advantage in these methods is to decrease the test cartridge processing time and to increase the analyzer throughput. Reducing the processing time also permits the testing of larger sample volumes, and hence, larger volumes of the pass-through conduit, which in turn minimizes the effect of the part to part variation of the volume of the pass-through conduit. This is particularly true where the volume of the pass-through conduit is less than 5 uL. Analyzer throughput is also dependent on the frame size and speed of the digital camera used. For example, 20,000 frames taken with a 15 frame-per-second (fps) camera may take approximately 23 minutes to scan the imaging chamber, but a 60 fps camera may take only 6 minutes. Increasing the size of the camera sensor would increase the field-of-view and reduce the scan time. There are tradeoffs in these changes, such as pixel size and the number of pixels. Larger pixels may result in a loss of resolution and smaller pixels may increase the noise. Decreasing the magnification would also increase the field-of-view and thus, reduce scan time. There are also tradeoffs here. For instance, if the magnification or numerical aperture is too low, platelets may not be recognized. Also, there may be a loss of resolution from projecting a lower magnification on the same size pixels. Where the mixture is not homogenous, or the changes in cell density from frame to frame are not relatively small, to ensure the accuracy of the CBC the preferred method is a complete counting of all the cells and platelets of the sample/diluent mixture in the imaging chamber.

The photometer and detector are used to measure the concentration of hemoglobin on whole blood in the photometric chamber, although in some embodiments this measurement could be carried out on the mixture of whole blood and diluent-stain in the imaging chamber. In this case, the dilution ratio needs to be known. The preferred method is to make the photometric measurement on whole blood. In another embodiment, the photometric chamber may contain a RBC lysing reagent for measuring the hemoglobin concentration. The lysing reagent may be provided in liquid or dried format. If in a liquid format, the lysing reagent may be supplied by a reagent blister, directly dispensed and sealed onto the test cartridge, or supplied from an external reagent supply. The lysing reagent may also contain a reagent for converting all of the hemoglobin to a particular form, such as methemoglobin, azide-methemoglobin, or cyanmethemoglobin. Examples of these reagents are sodium lauryl sulfate, sodium azide, or Drabkin's reagent.

The system is designed to ensure that unusual or clearly erroneous results, such as the presence of bubbles, clots, platelet clumps, abnormal cells or out-of-spec. readings, are rejected or flagged for human review.

Three basic cartridge designs, including variations, have been described, but many other cartridge configurations are possible. Different channel topologies and valve sequencing, for example, could be employed to accomplish the functionality described above. In many instances, fluids that are drawn by a negative pressure could instead be pushed by positive pressure, and vice versa. The cartridge-based system described above consists of a sample collection mechanism, valve, fluidic connections, imaging chamber, photometric chamber, and a mixing chamber. It is challenging to incorporate all of these features into the disposable cartridge at a commercially low cost. High-end multi-cavity injection molds can be used to obtain a low cost and high part-to-part repeatability. And while the system described above is designed to count blood cells, it could also be designed to analyze cells or other small particles in other types of biological media, such as cerebrospinal fluid (CSF), saliva, urine, or semen. The use of antibodies, such as CD4, CD34, CD61, or any other cell surface molecule could be used to identify specific cell types or subsets. Similarly, antibodies could be used for detecting bacterial, viral, or parasitic pathogens, antibodies for detecting erythrocyte precursors, circulating tumors, or leukemic cells or any combination thereof.

The system described above has been implemented in connection with special-purpose software programs, such as monitoring, control, and/or analysis software programs, running on one or more general-purpose computer platforms, but it could also be implemented with similar logic functionality embodied in whole or in part in special-purpose hardware. And while the system can be broken into the series of modules and steps shown for illustration purposes, one of ordinary skill in the art would recognize that it is also possible to combine them and/or split them differently to achieve a different breakdown, and that the functions of such modules and steps can be arbitrarily distributed and intermingled within different entities, such as differently housed machines, differently aggregated modules, or differently designed parts.

The present invention has now been described in connection with a number of specific embodiments thereof. However, numerous modifications, which are contemplated as falling within the scope of the present invention, should now be apparent to those skilled in the art. For example, there is room for significant variation in the arrangement of ports, chambers, and other fluidic elements in the different parts of the system, and fluid can be conveyed in different ways, such as by pumping, suction, or capillary action. It is therefore intended that the scope of the present invention be limited only by the scope of the claims appended hereto. In addition, the order of presentation of the claims should not be construed to limit the scope of any particular term in the claims.

What is claimed is:
1. A method of counting and analyzing biological particles, including cells and platelets, in whole blood comprising:
   a) measuring a predetermined volume of blood,
   b) mixing the volume of blood with an amount of diluent and/or stain to a substantially uniform mixture,
   c) transferring the mixture into an imaging chamber of fixed dimensions and of sufficient volume to receive the mixture and having a geometry, such that the particles in the mixture do not crowd or overlap when they settle to the bottom of the imagining chamber, whereby a monolayer of the particles is formed,
   d) taking digital images of all the particles in the monolayer with an automated microscope
   utilizing bright field and florescent imaging and having imaging processing software, to thereby obtain images of all of the particles in the measured volume of blood,
   e) counting all of at least one type of biological particle in all of the images, and f) deriving the number of the one type of particle per unit volume by dividing the number of the one type of particle in all the images by the volume of the blood sample.

2. A method of claim 1 further comprising analyzing the biological particles in the digital images with cell recognition software.

3. A method of claim 1 further comprising performing a differential of white cells in the blood sample.

4. A method of claim 1 further comprising displaying one or more digital images of the particles.

5. A method of claim 1 wherein a dilution ratio of diluent and/or stain to sample is between 10:1 and 250:1.

6. A method of claim 1 wherein the rate of transferring the mixture of diluent and/or stain and blood sample into the imaging chamber is such that the mixture remains substantially uniform.

7. A method of claim 1 wherein a depth of the imaging chamber is uniform and a shape of the imaging chamber in planar view is serpentine.

8. A method of claim 1 wherein the mixing includes the mixing the sample with diluent and stain.

9. A method of claim 1 wherein a geometry of the imaging chamber is such that a distribution of particles of the mixture remains substantially homogeneous when the mixture is transferred into the imaging chamber.

* * * * *